(12) United States Patent
Ji

(10) Patent No.: US 11,542,250 B2
(45) Date of Patent: Jan. 3, 2023

(54) INHIBITORS FOR THE β-CATENIN/B-CELL LYMPHOMA 9 (BCL9) PROTEIN-PROTEIN INTERACTION

(71) Applicant: H. LEE MOFFITT CANCER CENTER AND RESEARCH INSTITUTE, INC., Tampa, FL (US)

(72) Inventor: Haitao Ji, Tampa, FL (US)

(73) Assignee: H. Lee Moffitt Cancer Center and Research Institute, Inc., Tampa, FL (US)

(*) Notice: Subject to any disclaimer, the term of this patent is extended or adjusted under 35 U.S.C. 154(b) by 0 days.

(21) Appl. No.: 16/954,095

(22) PCT Filed: Dec. 17, 2018

(86) PCT No.: PCT/US2018/065963
§ 371 (c)(1),
(2) Date: Jun. 15, 2020

(87) PCT Pub. No.: WO2019/118961
PCT Pub. Date: Jun. 20, 2019

(65) Prior Publication Data
US 2021/0179583 A1    Jun. 17, 2021

Related U.S. Application Data

(60) Provisional application No. 62/599,322, filed on Dec. 15, 2017, provisional application No. 62/615,239, filed on Jan. 9, 2018.

(51) Int. Cl.
C07D 401/14    (2006.01)
C07D 401/12    (2006.01)

(52) U.S. Cl.
CPC ......... *C07D 401/14* (2013.01); *C07D 401/12* (2013.01)

(58) Field of Classification Search
None
See application file for complete search history.

(56) References Cited

U.S. PATENT DOCUMENTS

9,670,404 B2    6/2017    Xia et al.
2009/0092596 A1    4/2009    Haley et al.

FOREIGN PATENT DOCUMENTS

WO    2008071397 A1    6/2008
WO    2016168524 A1    10/2016

OTHER PUBLICATIONS

Zhang, M. et al. "Structure-Based Optimization of Small-Molecule Inhibitors for the β-Catenin/B-Cell Lymphoma 9 Protein-Protein Interaction" J. Med. Chem. 2018, 61, 2989-3007 (Year: 2018).*
International Search Report and Written Opinion in PCT/US2018/065963, dated Apr. 12, 2019. 11 pages.

* cited by examiner

*Primary Examiner* — Medhanit W Bahta
(74) *Attorney, Agent, or Firm* — Meunier Carlin & Curfman LLC

(57) ABSTRACT

Disclosed are inhibitors for the β-catenin/BCL9 interaction. The inhibitors are selective for β-catenin/BCL9 over β-catenin/cadherin interactions. Methods of using the disclosed compounds to treat cancer are also disclosed.

9 Claims, 1 Drawing Sheet

INHIBITORS FOR THE β-CATENIN/B-CELL LYMPHOMA 9 (BCL9) PROTEIN-PROTEIN INTERACTION

CROSS-REFERENCE TO RELATED APPLICATIONS

This application is a United States National Phase Patent Application of International Patent Application Number PCT/US2018/065963, filed on Dec. 17, 2018, which claims the benefit of priority to U.S. Provisional Application No. 62/599,322, filed Dec. 15, 2017, and U.S. Provisional Application No. 62/615,239, filed Jan. 9, 2018, the disclosures of which are incorporated herein by reference in their entireties.

ACKNOWLEDGEMENT OF GOVERNMENT SUPPORT

This invention was made with government support under Grant No. W81XWH-14-1-0083 awarded by the Department of Defense. The government has certain rights in the invention.

BACKGROUND

Hyperactivation of the canonical Wnt signaling pathway has been associated with the initiation and progression of triple negative breast cancers (TNBCs). This hyperactivation is mainly caused by the autocrine/paracrine activation of Wnt ligands and the epigenetic slicencing of Wnt antagonist genes, which results in accumulation of β-catenin in the cell nucleus and activates transcription of Wnt target genes. Wnt target genes initiate proliferation and metastasis of TNBC cells and self-renewal of TNBC stem cells. The formation of the β-catenin/B-cell lymphoma 9 (BCL9) complex in the cell nucleus is the penultimate step of canonical Wnt signaling. The aberrant formation of this protein-protein complex is a major driving force for TNBC tumorigenesis. The inhibition of the β-catenin/BCL9 interaction by small-molecule inhibitors represents an appealing therapeutic strategy. On the other hand, the surface area of β-catenin for binding with BCL9 is also used to bind cadherin. The β-catenin/cadherin interaction is essential for the integrity of epithelial junctions in normal cells. Therefore, the selectivity of small-molecule inhibitors for β-catenin/BCL9 over β-catenin/cadherin is important.

Stapled BCL9 L351-F374 α-helical peptides were designed to inhibit the β-catenin/BCL9 interaction (Kawamoto, et al. *J. Med Chem.* 2012, 55, 1137-1146; and Takada, et al. *Sci. Transl. Med* 2012, 4, 148ra117). The stapled peptides described in Kawamoto, et al *J. Med Chem.* 2012, 55, 1137-1146 did not exhibit cell-based activity. SAH-BCL9 described in Takada, et al. *Sci. Transl. Med* 2012, 4, 148ra117 was able to pass the cell membrane, bind with β-catenin, disrupt the β-catenin/BCL9 interaction, and selectively suppress transcription of Wnt target genes. This stapled peptide also inhibited tumor cell growth, angiogenesis, and metastasis without overt damage to normal tissues in the mouse xenograft models for colorectal carcinoma and multiple myeloma. However, the aqueous solubility, the immunogenic effects, and the in vivo stability of SAH-BCL9 were not reported.

Compound screening identified a small organic molecule, carnosic acid, that can disrupt the β-catenin/BCL9 interaction, inhibit β-catenin-dependent transcription, and destabilize activated β-catenin (de la Roche, et al. *Nature Commm.* 2012, 3, 680). Carnosic acid is a natural antioxidant and associated with many biological activities. Its catechol substructure readily reacts with protein nucleophiles after oxidation and has been recognized as a substructure for pan assay interference compounds (PAINS) (Baell and Holloway *J. Med Chem.* 2010, 53, 2719-2740; Beall and Walters *Nature* 2014, 513, 481-483). To date, no class-specific small-molecule inhibitors for the β-catenin/BCL9 interaction has been reported. Thus what are needed are new, potent and selective inhibitors for the β-catenin/BCL9 interaction and methods for their use. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to cancer therapy and to anticancer compounds. More specifically, the subject matter disclosed herein relates to inhibitors for the β-catenin/BCL9 interaction. Further, the subject matter disclosed herein relates to inhibitors that are selective for β-catenin/BCL9 over β-catenin/cadherin interactions. Also disclosed are methods of inhibiting the β-catenin/BCL9 interaction, as well as methods of treating certain cancers. In further aspects, the disclosed subject matter relates to a new benzaldehyde mediated photoredox reaction for the direct α-heteroarylation of amides and ethers. Still further, the disclosed subject matter relates to a HPLC/MS method for the determination of inhibitor cellular bioavailability.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 1A shows the surface model. FIG. 1B shows the stick model.

FIG. 2A shows the H-bond donor map (hatched). FIG. 2B shows the H-bond acceptor map (hatched).

DETAILED DESCRIPTION

Figure 1A:
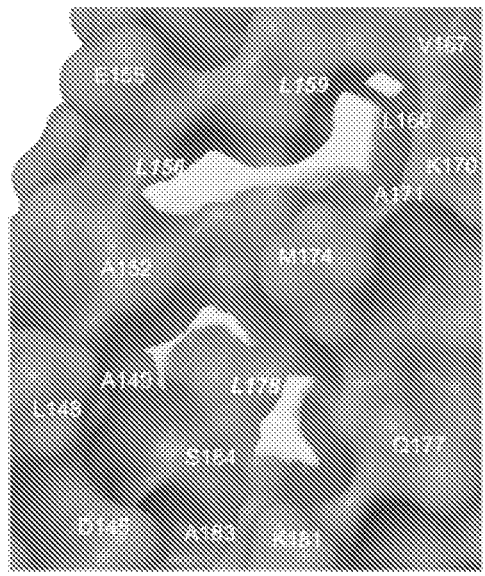
FIGS. 1A and 1B show results of the hydrophobic SiteMap analysis. The threshold of the SiteMap contour was set to −0.5 kcal/mol.
Figure 1B:
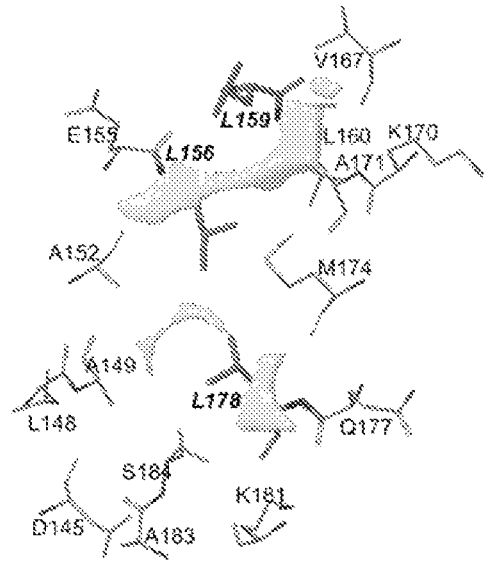
Figure 2A:
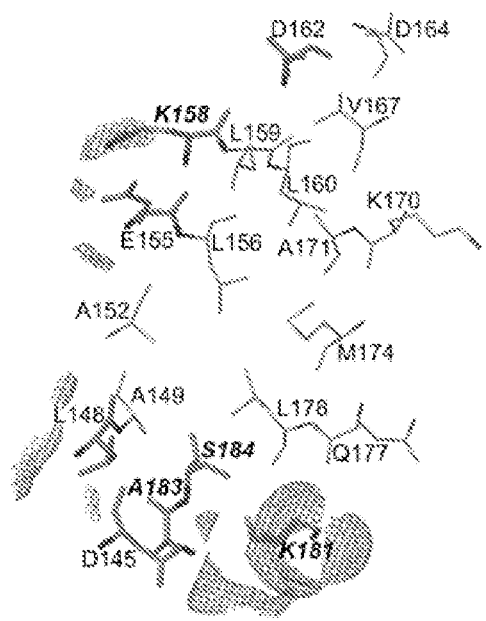
FIGS. 2A and 2B show results of H-bond SiteMap analysis. β-Catenin residues (PDB id, 2GL7) are shown green. The residues that contribute to the SiteMap contour are shaded by atom type. The threshold of the SiteMap contour was set to −8 kcal/mol.
Figure 2B:
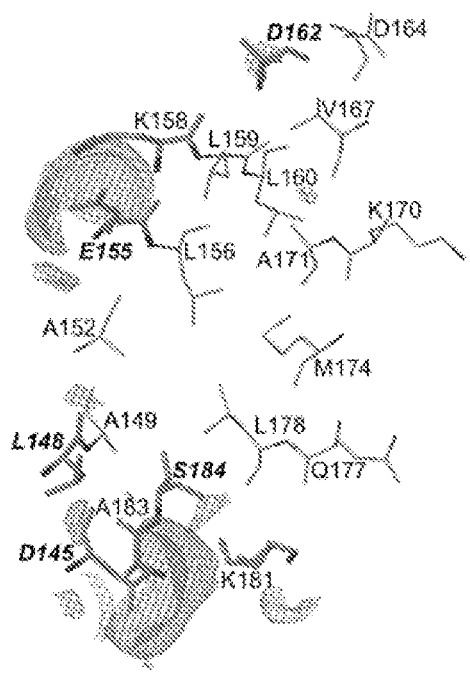

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds.

In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A^n$ is used herein as merely a generic substituent in the definitions below.

The term "alkoxy" as used herein is an alkyl group bound through a single, terminal ether linkage; that is, an "alkoxy" group can be defined as $-OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula $-C(O)H$. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O⁻.

The term "ester" as used herein is represented by the formula —OC(O)A¹ or —C(O)OA¹, where A¹ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula A¹OA², where A¹ and A² can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula A¹C(O)A², where A¹ and A² can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —NO₂.

The term "cyano" as used herein is represented by the formula —CN

The term "azido" as used herein is represented by the formula —N₃.

The term "sulfonyl" is used herein to refer to the sulfo-oxo group represented by the formula —S(O)₂A¹, where A¹ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)₂NH₂.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

In certain aspects, disclosed herein are compounds having Formula IA or IB.

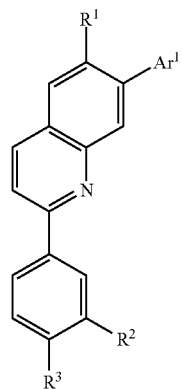

IA

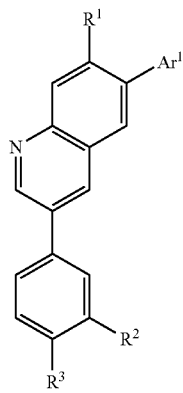

IB wherein
$R^1$ is selected from —($C_2$-$C_8$ alkyl)-OH, —($C_2$-$C_8$ alkyl)-$NH_2$, —O—($C_2$-$C_8$ alkyl)-OH, —O—($C_2$-$C_8$ alkyl)-$NH_2$, —NH—($C_2$-$C_8$ alkyl)-OH, —NH—($C_2$-$C_8$ alkyl)-$NH_2$, —NH-$Cy^1$, —NH-$Cy^2$, —O-$Cy^1$, —O-$Cy^2$, —NHCH$_2$-$Cy^1$, —NHCH$_2$-$Cy^2$, —OCH$_2$-$Cy^1$, and —OCH$_2$-$Cy^2$; wherein $Cy^1$, when present, is an amino $C_3$-$C_8$ cycloalkyl or hydroxy $C_3$-$C_8$ cycloalkyl, and wherein $Cy^1$ is substituted 0, 1, 2, or 3 groups independently selected from halogen, $C_1$-$C_4$ alkyl, $C_1$-$C_4$ monohaloalkyl, and $C_1$-$C_4$ polyhaloalkyl; and wherein $Cy^2$, when present, is a $C_2$-$C_7$ heterocycloalkyl comprising at least one oxygen or nitrogen atom, and wherein $Cy^2$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl;

$R^2$ is selected from $Ar^2$, -$A^1$-$A^2$-$Ar^2$, and —C≡C—$Ar^2$; wherein each of $A^1$ and $A^2$, when present, is independently selected from O, NH, and $CH_2$, provided that each of $A^1$ and $A^2$ is not simultaneously O; and wherein $Ar^2$ is selected from aryl and heteroaryl, and wherein $Ar^2$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, —NH-COR$^{20}$, —NHSO$_2$R$^{20}$, —CONR$^{21a}$R$^{21b}$, —SO$_2$NR$^{21a}$R$^{21b}$, —CO$_2$H, and tetrazole;

$R^3$ is selected from hydrogen, —($C_2$-$C_8$ alkyl)-OH, —($C_2$-$C_8$ alkyl)-$NH_2$, —O—($C_2$-$C_8$ alkyl)-OH, —O—($C_2$-$C_8$ alkyl)-$NH_2$, —NH—($C_2$-$C_8$ alkyl)-OH, and —NH—($C_2$-$C_8$ alkyl)-$NH_2$, —NH-$Cy^3$, —NH-$Cy^4$, —O-$Cy^3$, —O-$Cy^4$, —NHCH$_2$-$Cy^3$, —NHCH$_2$-$Cy^4$; —OCH$_2$-$Cy^3$, and —OCH$_2$-$Cy^4$; wherein $Cy^3$, when present, is an amino $C_3$-$C_8$ cycloalkyl or hydroxy $C_3$-$C_8$ cycloalkyl, and wherein $Cy^3$ is substituted 0, 1, 2, or 3 groups independently selected from halogen, $C_1$-$C_4$ alkyl, $C_1$-$C_4$ monohaloalkyl, and $C_1$-$C_4$ polyhaloalkyl; and wherein $Cy^4$, when present, is a $C_2$-$C_7$ heterocycloalkyl comprising at least one oxygen or nitrogen atom, and wherein $Cy^4$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl;

$Ar^1$ is selected from aryl and heteroaryl, and wherein $Ar^1$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, —NH-COR$^{20}$, —NHSO$_2$R$^{20}$, —CONR$^{21a}$R$^{21b}$, —SO$_2$NR$^{21a}$R$^{21b}$, —CO$_2$H, and tetrazole;

each occurrence of $R^{20}$, when present, is independently selected from $C_1$-$C_3$ alkyl, $C_1$-$C_3$ monohaloalkyl, $C_1$-$C_3$ polyhaloalkyl, and cyclopropyl;

each occurrence of $R^{21a}$ and $R^{21b}$, when present, is independently selected from hydrogen, $C_1$-$C_3$ alkyl, $C_1$-$C_3$ monohaloalkyl, $C_1$-$C_3$, and cyclopropyl;

or a pharmaceutically acceptable salt thereof.

In other aspects, disclosed herein are compounds having Formula II

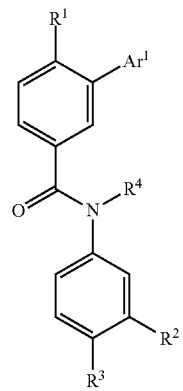

II wherein
$R^1$ is selected from —($C_2$-$C_8$ alkyl)-OH, —($C_2$-$C_8$ alkyl)-$NH_2$, —O—($C_2$-$C_8$ alkyl)-OH, —O—($C_2$-$C_8$ alkyl)-$NH_2$, —NH—($C_2$-$C_8$ alkyl)-OH, —NH—($C_2$-$C_8$ alkyl)-$NH_2$, —NH-$Cy^1$, —NH-$Cy^2$, —O-$Cy^1$, —O-$Cy^2$, —NHCH$_2$-$Cy^1$, —NHCH$_2$-$Cy^2$; —OCH$_2$-$Cy^1$, and —OCH$_2$-$Cy^2$; wherein $Cy^1$, when present, is an amino $C_3$-$C_8$ cycloalkyl or hydroxy $C_3$-$C_8$ cycloalkyl, and wherein $Cy^1$ is substituted 0, 1, 2, or 3 groups independently selected from halogen, $C_1$-$C_4$ alkyl, $C_1$-$C_4$ monohaloalkyl, and $C_1$-$C_4$ polyhaloalkyl; and wherein $Cy^2$, when present, is a $C_2$-$C_7$ heterocycloalkyl comprising at least one oxygen or nitrogen atom, and wherein $Cy^2$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl;

$R^2$ is selected from $Ar^2$, $-A^1$-$A^2$-$Ar^2$, and —C≡C—$Ar^2$; wherein each of $A^1$ and $A^2$, when present, is independently selected from O, NH, and $CH_2$, provided that each of $A^1$ and $A^2$ is not simultaneously O; and wherein $Ar^2$ is selected from aryl and heteroaryl, and wherein $Ar^2$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, —NHCOR$^{20}$, —NHSO$_2$R$^{20}$, —CONR$^{21a}$R$^{21b}$, —SO$_2$NR$^{21a}$R$^{21b}$, —CO$_2$H, and tetrazole;

$R^3$ is selected from hydrogen, —($C_2$-$C_8$ alkyl)-OH, —($C_2$-$C_8$ alkyl)-NH$_2$, —O—($C_2$-$C_8$ alkyl)-OH, —O—($C_2$-$C_8$ alkyl)-NH$_2$, —NH—($C_2$-$C_8$ alkyl)-OH, and —NH—($C_2$-$C_8$ alkyl)-NH$_2$, —NH-Cy$^3$, —NH-Cy$^4$, —O-Cy$^3$, —O-Cy$^4$, —NHCH$_2$-Cy$^3$, —NHCH$_2$-Cy$^4$; —OCH$_2$-Cy$^3$, and —OCH$_2$-Cy$^4$; wherein Cy$^3$, when present, is an amino $C_3$-$C_8$ cycloalkyl or hydroxy $C_3$-$C_8$ cycloalkyl, and wherein Cy$^3$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl; and wherein Cy$^4$, when present, is a $C_2$-$C_7$ heterocycloalkyl comprising at least one oxygen or nitrogen atom, and wherein Cy$^4$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl;

$R^4$ is selected from hydrogen and $C_1$-$C_4$ alkyl;

$Ar^1$ is selected from $C_5$-$C_7$ cycloalkyl, or $C_5$-$C_7$ cycloalkenyl, and wherein $Ar^1$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, —NHCOR$^{20}$, —NHSO$_2$R$^{20}$, —CONR$^{21a}$R$^{21b}$, —SO$_2$NR$^{21a}$R$^{21b}$, —CO$_2$H, and tetrazole;

each occurrence of $R^{20}$, when present, is independently selected from $C_1$-$C_3$ alkyl, $C_1$-$C_3$ monohaloalkyl, $C_1$-$C_3$ polyhaloalkyl, and cyclopropyl;

each occurrence of $R^{21a}$ and $R^{21b}$, when present, is independently selected from hydrogen, $C_1$-$C_3$ alkyl, $C_1$-$C_3$ monohaloalkyl, $C_1$-$C_3$, and cyclopropyl;

or a pharmaceutically acceptable salt thereof.

Also disclosed are pharmaceutical compositions comprising a therapeutically effective amount of a disclosed compound of formula IA, IB, or II, or a pharmaceutically acceptable salt thereof, and a pharmaceutically acceptable carrier.

In one aspect, each of $A^1$ and $A^2$, when present, is independently selected from O, NH, and $CH_2$, provided that each of $A^1$ and $A^2$ is simultaneously O. In a further aspect, each of $A^1$ and $A^2$, when present, is independently selected from O and NH. In a still further aspect, each of $A^1$ and $A^2$, when present, is independently selected from O and $CH_2$. In yet a further aspect, each of $A^1$ and $A^2$, when present, is independently selected from NH and $CH_2$. In a still further aspect, each of $A^1$ and $A^2$, when present, is NH. In yet a further aspect, each of $A^1$ and $A^2$, when present, is $CH_2$.

In one aspect, $R^1$ is selected from —($C_2$-$C_8$ alkyl)-OH, —($C_2$-$C_8$ alkyl)-NH$_2$, —O—($C_2$-$C_8$ alkyl)-OH, —O—($C_2$-$C_8$ alkyl)-NH$_2$, —NH—($C_2$-$C_8$ alkyl)-OH, —NH—($C_2$-$C_8$ alkyl)-NH$_2$, —NH-Cy$^1$, —NH-Cy$^2$, —O-Cy$^1$, —O-Cy$^2$, —NHCH$_2$-Cy$^1$, —NHCH$_2$-Cy$^2$; —OCH$_2$-Cy$^1$, and —OCH$_2$-Cy$^2$. In a further aspect, $R^1$ is selected from —($C_2$-$C_4$ alkyl)-OH, —($C_2$-$C_4$ alkyl)-NH$_2$, —O—($C_2$-$C_4$ alkyl)-OH, —O—($C_2$-$C_4$ alkyl)-NH$_2$, —NH—($C_2$-$C_4$ alkyl)-OH, —NH—($C_2$-$C_4$ alkyl)-NH$_2$, —NH-Cy$^1$, —NH-Cy$^2$, —O-Cy$^1$, —O-Cy$^2$, —NHCH$_2$-Cy$^1$, —NHCH$_2$-Cy$^2$; —OCH$_2$-Cy$^1$, and —OCH$_2$-Cy$^2$.

In a further aspect, $R^1$ is selected from —($C_2$-$C_8$ alkyl)-OH, —O—($C_2$-$C_8$ alkyl)-OH, —O—($C_2$-$C_8$ alkyl)-NH$_2$, —O-Cy$^1$, —O-Cy$^2$, —OCH-Cy$^1$, and —OCH$_2$-Cy$^2$. In a still further aspect, $R^1$ is selected from —($C_2$-$C_8$ alkyl)-OH, —O—($C_2$-$C_8$ alkyl)-OH, and —O—($C_2$-$C_8$ alkyl)-NH$_2$. In yet a further aspect, $R^1$ is —($C_2$-$C_8$ alkyl)-OH. In an even further aspect, $R^1$ is —O—($C_2$-$C_8$ alkyl)-OH. In a still further aspect, $R^1$ is —O—($C_2$-$C_8$ alkyl)-NH$_2$.

In a further aspect, $R^1$ is selected from —O-Cy$^1$, —O-Cy$^2$, —OCH$_2$-Cy$^1$, and —OCH$_2$—Cy$^2$. In a still further aspect, $R^1$ is selected from —O-Cy$^1$ and —O-Cy$^2$. In yet a further aspect, $R^1$ is selected from —OCH$_2$-Cy$^1$ and —OCH$_2$-Cy$^2$. In an even further aspect, $R^2$ is —O-Cy$^1$. In a still further aspect, $R^1$ is —O-Cy$^2$. In yet a further aspect, $R^1$ is —OCH$_2$-Cy$^1$. In an even further aspect, $R^1$ is —OCH$_2$-Cy$^2$.

In a further aspect, $R^1$ is selected from —($C_2$-$C_8$ alkyl)-NH$_2$, —NH—($C_2$-$C_8$ alkyl)-OH, —NH—($C_2$-$C_8$ alkyl)-NH$_2$, —NH-Cy$^1$, —NH-Cy$^2$, —NHCH$_2$-Cy$^1$, and —NHCH$_2$-Cy$^2$. In a still further aspect, $R^1$ is selected from —($C_2$-$C_8$ alkyl)-NH$_2$, —NH—($C_2$-$C_8$ alkyl)-OH, and —NH—($C_2$-$C_8$ alkyl)-NH$_2$. In yet a further aspect, $R^1$ is —($C_2$-$C_8$ alkyl)-NH$_2$. In an even further aspect, $R^1$ is —NH—($C_2$-$C_8$ alkyl)-OH. In a still further aspect, $R^1$ is —NH—($C_2$-$C_8$ alkyl)-NH$_2$.

In a further aspect, $R^1$ is selected from —NH-Cy$^1$, —NH-Cy$^2$, —NHCH$_2$-Cy$^1$, and —NHCH$_2$-Cy$^2$. In a still further aspect, $R^1$ is selected from —NH-Cy$^1$ and —NH-Cy$^2$. In yet a further aspect, $R^1$ is —NH-Cy$^1$. In an even further aspect, $R^1$ is —NH-Cy$^2$. In a still further aspect, $R^1$ is selected from —NHCH$_2$-Cy$^1$ and —NHCH$_2$-Cy$^2$. In yet a further aspect, $R^1$ is —NHCH$_2$-Cy$^1$. In an even further aspect, $R^1$ is —NHCH$_2$-Cy$^2$.

In a further aspect, $R^1$ is selected from —NH-Cy$^1$, —NH-Cy$^2$, —O-Cy$^1$, —O-Cy$^2$, —NHCH$_2$-Cy$^1$, —NHCH$_2$-Cy$^2$; —OCH$_2$-Cy$^1$, and —OCH$_2$-Cy$^2$.

In a further aspect, $R^1$ is selected from —($C_2$-$C_8$ alkyl)-OH, —($C_2$-$C_8$ alkyl)-NH$_2$, —O—($C_2$-$C_8$ alkyl)-OH, —O—($C_2$-$C_8$ alkyl)-NH$_2$, —NH—($C_2$-$C_8$ alkyl)-OH, and —NH—($C_2$-$C_8$ alkyl)-NH$_2$.

In one aspect, $R^2$ is selected from $Ar^2$, -$A^1$-$A^2$-$Ar^2$, and C≡C—$Ar^2$. In a still further aspect, $R^2$ is selected from $Ar^2$ and C≡C—$Ar^2$. In yet a further aspect, $R^2$ is selected from $Ar^2$ and -$A^1$-$A^2$-$Ar^2$. In an even further aspect, $R^2$ is selected from -$A^1$-$A^2$-$Ar^2$ and C≡C—$Ar^2$. In a still further aspect, $R^2$ is C≡C—$Ar^2$. In yet a further aspect, $R^2$ is -$A^1$-$A^2$-$Ar^2$. In an even further aspect, $R^2$ is $Ar^2$.

In one aspect, $R^3$ is selected from hydrogen, —($C_2$-$C_8$ alkyl)-OH, —($C_2$-$C_8$ alkyl)-NH$_2$, —O—($C_2$-$C_8$ alkyl)-OH, —O—($C_2$-$C_8$ alkyl)-NH$_2$, —NH—($C_2$-$C_8$ alkyl)-OH, and —NH—($C_2$-$C_8$ alkyl)-NH$_2$, —NH-Cy$^3$, —NH-Cy$^4$, —O-Cy$^3$, —O-Cy$^4$, —NHCH$_2$-Cy$^3$, —NHCH$_2$-Cy$^4$; —OCH$_2$-Cy$^3$, and —OCH$_2$-Cy$^4$. In a further aspect, $R^3$ is selected from hydrogen, —($C_2$-$C_4$ alkyl)-OH, —($C_2$-$C_4$ alkyl)-NH$_2$, —O—($C_2$-$C_4$ alkyl)-OH, —O—($C_2$-$C_4$ alkyl)-NH$_2$, —NH—($C_2$-$C_4$ alkyl)-OH, and —NH—($C_2$-$C_4$ alkyl)-NH$_2$, —NH-Cy$^3$, —NH-Cy$^4$, —O-Cy$^3$, —O-Cy$^4$, —NHCH$_2$-Cy$^3$, —NHCH$_2$-Cy$^4$; —OCH$_2$-Cy$^3$, and —OCH$_2$-Cy$^4$.

In a further aspect, $R^3$ is selected from —($C_2$-$C_8$ alkyl)-OH, —O—($C_2$-$C_8$ alkyl)-OH, —O—($C_2$-$C_8$ alkyl)-NH$_2$, —O-Cy$^3$, —O-Cy$^4$, —OCH$_2$-Cy$^3$, and —OCH$_2$-Cy$^4$. In a still further aspect, $R^3$ is selected from —($C_2$-$C_8$ alkyl)-OH, —O—($C_2$-$C_8$ alkyl)-OH, and —O—($C_2$-$C_8$ alkyl)-$NH_2$. In yet a further aspect, $R^3$ is —($C_2$-$C_8$ alkyl)-OH. In an even further aspect, $R^3$ is —O—($C_2$-$C_8$ alkyl)-OH. In a still further aspect, $R^3$ is —O—($C_2$-$C_8$ alkyl)-$NH_2$.

In a further aspect, $R^3$ is selected from —O-$Cy^3$, —O-$Cy^4$, —$OCH_2$-$Cy^3$, and —$OCH_2$—$Cy^4$. In a still further aspect, $R^3$ is selected from —O-$Cy^3$ and —O-$Cy^4$. In yet a further aspect, $R^3$ is selected from —$OCH_2$-$Cy^3$ and —$OCH_2$-$Cy^4$. In an even further aspect, $R^3$ is —O-$Cy^3$. In a still further aspect, $R^3$ is —O-$Cy^4$. In yet a further aspect, $R^3$ is —$OCH_2$-$Cy^3$. In an even further aspect, $R^3$ is —$OCH_2$-$Cy^4$.

In a further aspect, $R^3$ is selected from —($C_2$-$C_8$ alkyl)-$NH_2$, —NH—($C_2$-$C_8$ alkyl)-OH, —NH—($C_2$-$C_8$ alkyl)-$NH_2$, —NH-$Cy^3$, —NH-$Cy^4$, —$NHCH_2$-$Cy^3$, and —$NHCH_2$-$Cy^4$. In a still further aspect, $R^3$ is selected from —($C_2$-$C_8$ alkyl)-$NH_2$, —NH—($C_2$-$C_8$ alkyl)-OH, and —NH—($C_2$-$C_8$ alkyl)-$NH_2$. In yet a further aspect, $R^3$ is —($C_2$-$C_8$ alkyl)-$NH_2$. In an even further aspect, $R^3$ is —NH—($C_2$-$C_8$ alkyl)-OH. In a still further aspect, $R^3$ is —NH—($C_2$-$C_8$ alkyl)-$NH_2$.

In a further aspect, $R^3$ is selected from —NH-$Cy^3$, —NH-$Cy^4$, —$NHCH_2$-$Cy^3$, and —$NHCH_2$-$Cy^4$. In a still further aspect, $R^3$ is selected from —NH-$Cy^3$ and —NH-$Cy^4$. In yet a further aspect, $R^3$ is —NH-$Cy^3$. In an even further aspect, $R^3$ is —NH-$Cy^4$. In a still further aspect, $R^3$ is selected from —$NHCH_2$-$Cy^3$ and —$NHCH_2$-$Cy^4$. In yet a further aspect, $R^3$ is —$NHCH_2$-$Cy^3$. In an even further aspect, $R^3$ is —$NHCH_2$-$Cy^4$.

In a further aspect, $R^3$ is selected from —NH-$Cy^3$, —NH-$Cy^4$, —O-$Cy^3$, —O-$Cy^4$, —$NHCH_2$-$Cy^3$, —$NHCH_2$-$Cy^4$; —$OCH_2$-$Cy^3$, and —$OCH_2$-$Cy^4$.

In a further aspect, $R^3$ is selected from —($C_2$-$C_8$ alkyl)-OH, —($C_2$-$C_8$ alkyl)-$NH_2$, —O—($C_2$-$C_8$ alkyl)-OH, —O—($C_2$-$C_8$ alkyl)-$NH_2$, —NH—($C_2$-$C_8$ alkyl)-OH, and —NH—($C_2$-$C_8$ alkyl)-$NH_2$.

In further aspects, $R^4$ is hydrogen.

In one aspect, each occurrence of $R^{20}$, when present, is independently selected from $C_1$-$C_3$ alkyl, $C_1$-$C_3$ monohaloalkyl, $C_1$-$C_3$ polyhaloalkyl, and cyclopropyl. In a further aspect, each occurrence of $R^{20}$, when present, is independently selected from $C_1$-$C_3$ alkyl. In a still further aspect, each occurrence of $R^{20}$, when present, is independently selected from $C_1$-$C_3$ monohaloalkyl. In yet a further aspect, each occurrence of $R^{20}$, when present, is independently selected from $C_1$-$C_3$ polyhaloalkyl.

In a further aspect, each occurrence of $R^{20}$, when present, is independently selected from methyl, ethyl, —$CH_2F$, —$CH_2Cl$, —$CH_2CH_2F$, —$CH_2CH_2Cl$, —$CHF_2$, —$CF_3$, —CHCF, —$CCl_3$, —$CH_2CHF_2$, —$CH_2CF_3$, —$CH_2CHCl_2$, and —$CH_2CCl_3$. In a still further aspect, each occurrence of $R^{20}$, when present, is independently selected from methyl, —$CH_2F$, —$CHF_2$, —$CF_3$, —$CHCl_2$, and —$CCl_3$. In yet a further aspect, each occurrence of $R^{20}$, when present, is independently selected from methyl, ethyl, —$CH_2F$, —$CH_2CH_2F$, —$CHF_2$, —$CF_3$, —$CH_2CHF_2$, and —$CH_2CF_3$. In an even further aspect, each occurrence of $R^{20}$, when present, is independently selected from methyl, —$CH_2F$, —$CHF_2$, and —$CF_3$.

In one aspect, each occurrence of $R^{20}$, when present, is independently selected from $C_1$-$C_3$ alkyl, $C_1$-$C_3$ monohaloalkyl, $C_1$-$C_3$ polyhaloalkyl, and cyclopropyl. In a further aspect, each occurrence of $R^{20}$, when present, is independently selected from $C_1$-$C_3$ alkyl. In a still further aspect, each occurrence of $R^{20}$, when present, is independently selected from $C_1$-$C_3$ monohaloalkyl. In yet a further aspect, each occurrence of $R^{20}$, when present, is independently selected from $C_1$-$C_3$ polyhaloalkyl.

In a further aspect, each occurrence of $R^{20}$, when present, is independently selected from methyl, ethyl, —$CH_2F$, —$CH_2Cl$, —$CH_2CH_2F$, —$CH_2CH_2Cl$, —$CHF_2$, —$CF_3$, —CHCF, —$CCl_3$, —$CH_2CHF_2$, —$CH_2CF_3$, —$CH_2CHCl_2$, and —$CH_2CCl_3$. In a still further aspect, each occurrence of $R^{20}$, when present, is independently selected from methyl, —$CH_2F$, —$CHF_2$, —$CF_3$, —$CHCl_2$, and —$CCl_3$. In yet a further aspect, each occurrence of $R^{20}$, when present, is independently selected from methyl, ethyl, —$CH_2F$, —$CH_2CH_2F$, —$CHF_2$, —$CF_3$, —$CH_2CHF_2$, and —$CH_2CF_3$. In an even further aspect, each occurrence of $R^{20}$, when present, is independently selected from methyl, —$CH_2F$, —$CHF_2$, and —$CF_3$.

In one aspect, each occurrence of $R^{21a}$ and $R^{21b}$, when present, is independently selected from hydrogen, $C_1$-$C_3$ alkyl, $C_1$-$C_3$ monohaloalkyl, $C_1$-$C_3$ polyhaloalkyl, and cyclopropyl. In a further aspect, each occurrence of $R^{21a}$ and $R^{21b}$, when present, is independently selected from hydrogen and $C_1$-$C_3$ alkyl. In a still further aspect, each occurrence of $R^{21a}$ and $R^{21b}$, when present, is independently selected from hydrogen and $C_1$-$C_3$ monohaloalkyl. In yet a further aspect, each occurrence of $R^{21a}$ and $R^{21b}$, when present, is independently selected from hydrogen and $C_1$-$C_4$ polyhaloalkyl. In an even further aspect, each occurrence of $R^{21a}$ and $R^{21b}$, when present, is hydrogen.

In a further aspect, each occurrence of $R^{21a}$ and $R^{21b}$, when present, is independently selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a still further aspect, each occurrence of $R^{21a}$ and $R^{21b}$, when present, is independently selected from hydrogen, methyl, —$CH_2F$, —$CHF_2$, —$CF_3$, —$CHCl_2$, and —$CCl_3$. In yet a further aspect, each occurrence of $R^{21a}$ and $R^{21b}$, when present, is independently selected from hydrogen, methyl, ethyl, —$CH_2F$, —$CH_2CH_2F$, —$CHF_2$, —$CF_3$, —$CH_2CHF_2$, and —$CH_2CF_3$. In an even further aspect, each occurrence of $R^{21a}$ and $R^{21b}$, when present, is independently selected from hydrogen, methyl, —$CH_2F$, —$CHF_2$, and —$CF_3$.

In one aspect, $Cy^1$, when present, is an amino $C_3$-$C_8$ cycloalkyl or hydroxy $C_3$-$C_8$ cycloalkyl, and wherein $Cy^1$ is substituted 0, 1, 2, or 3 groups independently selected from halogen, $C_1$-$C_4$ alkyl, $C_1$-$C_4$ monohaloalkyl, and $C_1$-$C_4$ polyhaloalkyl.

In one aspect, $Cy^2$, when present, is a $C_2$-$C_7$ heterocycloalkyl comprising at least one oxygen or nitrogen atom, and wherein $Cy^2$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl. In a further aspect, $Cy^2$, when present, is a $C_2$-$C_7$ heterocycloalkyl comprising at least one oxygen or nitrogen atom, and wherein $Cy^2$ is substituted with 0, 1, or 2 groups independently selected from halogen, $C_1$-$C_4$ alkyl, $C_1$-$C_4$ monohaloalkyl, and $C_1$-$C_4$ polyhaloalkyl. In a still further aspect, $Cy^2$, when present, is a $C_2$-$C_7$ heterocycloalkyl comprising at least one oxygen or nitrogen atom, and wherein $Cy^2$ is substituted with 0 or 1 group selected from halogen, $C_1$-$C_4$ alkyl, $C_1$-$C_4$ monohaloalkyl, and $C_1$-$C_4$ polyhaloalkyl. In yet a further aspect, $Cy^2$, when present, is a $C_2$-$C_7$ heterocycloalkyl comprising at least one oxygen or nitrogen atom, and wherein $Cy^2$ is monosubstituted with a group selected from halogen, $C_1$-$C_4$ alkyl, $C_1$-$C_4$ monohaloalkyl, and $C_1$-$C_4$ polyhaloalkyl. In an even further aspect, $Cy^2$, when present, is an unsubstituted $C_2$-$C_7$ heterocycloalkyl comprising at least one oxygen or nitrogen atom.

In a further aspect, $Cy^2$, when present, is a $C_2$-$C_6$ heterocycloalkyl comprising at least one oxygen or nitrogen atom, and wherein $Cy^2$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl. In a still further aspect, $Cy^2$, when present, is a $C_2$-$C_6$ heterocycloalkyl comprising at least one oxygen or nitrogen atom, and wherein $Cy^2$ is substituted with 0, 1, or 2 groups independently selected from halogen, $C_1$-$C_4$ alkyl, $C_1$-$C_4$ monohaloalkyl, and $C_1$-$C_4$ polyhaloalkyl. In yet a further aspect, $Cy^2$, when present, is a $C_2$-$C_6$ heterocycloalkyl comprising at least one oxygen or nitrogen atom, and wherein $Cy^2$ is substituted with 0 or 1 group selected from halogen, $C_1$-$C_4$ alkyl, $C_1$-$C_4$ monohaloalkyl, and $C_1$-$C_4$ polyhaloalkyl. In an even further aspect, $Cy^2$, when present, is a $C_2$-$C_6$ heterocycloalkyl comprising at least one oxygen or nitrogen atom, and wherein $Cy^2$ is monosubstituted with a group selected from halogen, $C_1$-$C_4$ alkyl, $C_1$-$C_4$ monohaloalkyl, and $C_1$-$C_4$ polyhaloalkyl. In a still further aspect, $Cy^2$, when present, is an unsubstituted $C_2$-$C_6$ heterocycloalkyl comprising at least one oxygen or nitrogen atom.

In a further aspect, $Cy^2$, when present, is a $C_2$-$C_5$ heterocycloalkyl comprising at least one oxygen or nitrogen atom, and wherein $Cy^2$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl. In a still further aspect, $Cy^2$, when present, is a $C_2$-$C_5$ heterocycloalkyl comprising at least one oxygen or nitrogen atom, and wherein $Cy^2$ is substituted with 0, 1, or 2 groups independently selected from halogen, $C_1$-$C_4$ alkyl, $C_1$-$C_4$ monohaloalkyl, and $C_1$-$C_4$ polyhaloalkyl. In yet a further aspect, $Cy^2$, when present, is a $C_2$-$C_5$ heterocycloalkyl comprising at least one oxygen or nitrogen atom, and wherein $Cy^2$ is substituted with 0 or 1 group selected from halogen, $C_1$-$C_4$ alkyl, $C_1$-$C_4$ monohaloalkyl, and $C_1$-$C_4$ polyhaloalkyl. In an even further aspect, $Cy^2$, when present, is a $C_2$-$C_5$ heterocycloalkyl comprising at least one oxygen or nitrogen atom, and wherein $Cy^2$ is monosubstituted with a group selected from halogen, $C_1$-$C_4$ alkyl, $C_1$-$C_4$ monohaloalkyl, and $C_1$-$C_4$ polyhaloalkyl. In a still further aspect, $Cy^2$, when present, is an unsubstituted $C_2$-$C_5$ heterocycloalkyl comprising at least one oxygen or nitrogen atom.

In a further aspect, $Cy^2$, when present, is a $C_2$-$C_4$ heterocycloalkyl comprising at least one oxygen or nitrogen atom, and wherein $Cy^2$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl. In a still further aspect, $Cy^2$, when present, is a $C_2$-$C_4$ heterocycloalkyl comprising at least one oxygen or nitrogen atom, and wherein $Cy^2$ is substituted with 0, 1, or 2 groups independently selected from halogen, $C_1$-$C_4$ alkyl, $C_1$-$C_4$ monohaloalkyl, and $C_1$-$C_4$ polyhaloalkyl. In yet a further aspect, $Cy^2$, when present, is a $C_2$-$C_4$ heterocycloalkyl comprising at least one oxygen or nitrogen atom, and wherein $Cy^2$ is substituted with 0 or 1 group selected from halogen, $C_1$-$C_4$ alkyl, $C_1$-$C_4$ monohaloalkyl, and $C_1$-$C_4$ polyhaloalkyl. In an even further aspect, $Cy^2$, when present, is a $C_2$-$C_4$ heterocycloalkyl comprising at least one oxygen or nitrogen atom, and wherein $Cy^2$ is monosubstituted with a group selected from halogen, $C_1$-$C_4$ alkyl, $C_1$-$C_4$ monohaloalkyl, and $C_1$-$C_4$ polyhaloalkyl. In a still further aspect, $Cy^2$, when present, is an unsubstituted $C_2$-$C_4$ heterocycloalkyl comprising at least one oxygen or nitrogen atom.

In a further aspect, $Cy^2$, when present, is a $C_4$ heterocycloalkyl comprising at least one oxygen or nitrogen atom, and wherein $Cy^2$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl. In a still further aspect, $Cy^2$, when present, is a $C_4$ heterocycloalkyl comprising at least one oxygen or nitrogen atom, and wherein $Cy^2$ is substituted with 0, 1, or 2 groups independently selected from halogen, $C_1$-$C_4$ alkyl, $C_1$-$C_4$ monohaloalkyl, and $C_1$-$C_4$ polyhaloalkyl. In yet a further aspect, $Cy^2$, when present, is a $C_4$ heterocycloalkyl comprising at least one oxygen or nitrogen atom, and wherein $Cy^2$ is substituted with 0 or 1 group selected from halogen, $C_1$-$C_4$ alkyl, $C_1$-$C_4$ monohaloalkyl, and $C_1$-$C_4$ polyhaloalkyl. In an even further aspect, $Cy^2$, when present, is a $C_4$ heterocycloalkyl comprising at least one oxygen or nitrogen atom, and wherein $Cy^2$ is monosubstituted with a group selected from halogen, $C_1$-$C_4$ alkyl, $C_1$-$C_4$ monohaloalkyl, and $C_1$-$C_4$ polyhaloalkyl. In a still further aspect, $Cy^2$, when present, is an unsubstituted $C_4$ heterocycloalkyl comprising at least one oxygen or nitrogen atom.

In a further aspect, $Cy^2$, when present, is pyrrolidinyl substituted with 0, 1, 2, or 3 groups independently selected from halogen, $C_1$-$C_4$ alkyl, $C_1$-$C_4$ monohaloalkyl, and $C_1$-$C_4$ polyhaloalkyl. In a still further aspect, $Cy^2$, when present, is pyrrolidinyl substituted with 0, 1, or 2 groups independently selected from halogen, $C_1$-$C_4$ alkyl, $C_1$-$C_4$ monohaloalkyl, and $C_1$-$C_4$ polyhaloalkyl. In yet a further aspect, $Cy^2$, when present, is pyrrolidinyl substituted with 0 or 1 group selected from halogen, $C_1$-$C_4$ alkyl, $C_1$-$C_4$ monohaloalkyl, and $C_1$-$C_4$ polyhaloalkyl. In an even further aspect, $Cy^2$, when present, is pyrrolidinyl monosubstituted with a group selected from halogen, $C_1$-$C_4$ alkyl, $C_1$-$C_4$ monohaloalkyl, and $C_1$-$C_4$ polyhaloalkyl. In a still further aspect, $Cy^2$, when present, is an unsubstituted pyrrolidinyl.

In a further aspect, $Cy^2$, when present, is pyrrolidinyl substituted with 0, 1, 2, or 3 groups independently selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a still further aspect, $Cy^2$, when present, is pyrrolidinyl substituted with 0, 1, or 2 groups independently selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $Cy^2$, when present, is pyrrolidinyl substituted with 0 or 1 group selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In an even further aspect, $Cy^2$, when present, is pyrrolidinyl monosubstituted with a group selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$.

In a further aspect, $Cy^2$, when present, is pyrrolidinyl substituted with 0, 1, 2, or 3 groups independently selected from —F, —Cl, methyl, —$CH_2F$, —$CH_2Cl$, —$CHF_2$, —$CF_3$, —$CHCl_2$, and —$CCl_3$. In a still further aspect, $Cy^2$, when present, is pyrrolidinyl substituted with 0, 1, or 2 groups independently selected from —F, —Cl, methyl, —$CH_2F$, —$CH_2Cl$, —$CHF_2$, —$CF_3$, —$CHCl_2$, and —$CCl_3$. In yet a further aspect, $Cy^2$, when present, is pyrrolidinyl substituted with 0 or 1 group selected from —F, —Cl, methyl, —$CH_2F$, —$CH_2Cl$, —$CHF_2$, —$CF_3$, —$CHCl_2$, and —$CCl_3$. In an even further aspect, $Cy^2$, when present, is pyrrolidinyl monosubstituted with a group selected from —F, —Cl, methyl, —$CH_2F$, —$CH_2Cl$, —$CHF_2$, —$CF_3$, —$CHCl_2$, and —$CCl_3$.

In a further aspect, $Cy^2$, when present, is pyrrolidinyl substituted with 0, 1, 2, or 3 groups independently selected from —F, methyl, —CH$_2$F, —CHF$_2$, and —CF$_3$. In a still further aspect, Cy$^2$, when present, is pyrrolidinyl substituted with 0, 1, or 2 groups independently selected from —F, methyl, —CH$_2$F, —CHF$_2$, and —CF$_3$. In yet a further aspect, Cy$^2$, when present, is pyrrolidinyl substituted with 0 or 1 group selected from —F, methyl, —CH$_2$F, —CHF$_2$, and —CF$_3$. In an even further aspect, Cy$^2$, when present, is pyrrolidinyl monosubstituted with a group selected from —F, methyl, —CH$_2$F, —CHF$_2$, and —CF$_3$.

In one aspect, Cy$^3$, when present, is an amino C$_3$-C$_8$ cycloalkyl or hydroxy C$_3$-C$_8$ cycloalkyl, and wherein Cy$^3$ is substituted 0, 1, 2, or 3 groups independently selected from halogen, C$_1$-C$_4$ alkyl, C$_1$-C$_4$ monohaloalkyl, and C$_1$-C$_4$ polyhaloalkyl.

In one aspect, Cy$^4$, when present, is a C$_2$-C$_7$ heterocycloalkyl comprising at least one oxygen or nitrogen atom, and wherein Cy$^4$ is substituted with 0, 1, 2, or 3 groups independently selected from halogen, C$_1$-C$_4$ alkyl, C$_1$-C$_4$ monohaloalkyl, and C$_1$-C$_4$ polyhaloalkyl. In a further aspect, Cy$^4$, when present, is a C$_2$-C$_7$ heterocycloalkyl comprising at least one oxygen or nitrogen atom, and wherein Cy$^4$ is substituted with 0, 1, or 2 groups independently selected from halogen, C$_1$-C$_4$ alkyl, C$_1$-C$_4$ monohaloalkyl, and C$_1$-C$_4$ polyhaloalkyl. In a still further aspect, Cy$^4$, when present, is a C$_2$-C$_7$ heterocycloalkyl comprising at least one oxygen or nitrogen atom, and wherein Cy$^4$ is substituted with 0 or 1 group selected from halogen, C$_1$-C$_4$ alkyl, C$_1$-C$_4$ monohaloalkyl, and C$_1$-C$_4$ polyhaloalkyl. In yet a further aspect, Cy$^4$, when present, is a C$_2$-C$_7$ heterocycloalkyl comprising at least one oxygen or nitrogen atom, and wherein Cy$^4$ is monosubstituted with a group selected from halogen, C$_1$-C$_4$ alkyl, C$_1$-C$_4$ monohaloalkyl, and C$_1$-C$_4$ polyhaloalkyl. In an even further aspect, Cy$^4$, when present, is an unsubstituted C$_2$-C$_7$ heterocycloalkyl comprising at least one oxygen or nitrogen atom.

In a further aspect, Cy$^4$, when present, is a C$_2$-C$_6$ heterocycloalkyl comprising at least one oxygen or nitrogen atom, and wherein Cy$^4$ is substituted with 0, 1, 2, or 3 groups independently selected from halogen, C$_1$-C$_4$ alkyl, C$_1$-C$_4$ monohaloalkyl, and C$_1$-C$_4$ polyhaloalkyl. In a still further aspect, Cy$^4$, when present, is a C$_2$-C$_6$ heterocycloalkyl comprising at least one oxygen or nitrogen atom, and wherein Cy$^4$ is substituted with 0, 1, or 2 groups independently selected from halogen, C$_1$-C$_4$ alkyl, C$_1$-C$_4$ monohaloalkyl, and C$_1$-C$_4$ polyhaloalkyl. In yet a further aspect, Cy$^4$, when present, is a C$_2$-C$_6$ heterocycloalkyl comprising at least one oxygen or nitrogen atom, and wherein Cy$^4$ is substituted with 0 or 1 group selected from halogen, C$_1$-C$_4$ alkyl, C$_1$-C$_4$ monohaloalkyl, and C$_1$-C$_4$ polyhaloalkyl. In an even further aspect, Cy$^4$, when present, is a C$_2$-C$_6$ heterocycloalkyl comprising at least one oxygen or nitrogen atom, and wherein Cy$^4$ is monosubstituted with a group selected from halogen, C$_1$-C$_4$ alkyl, C$_1$-C$_4$ monohaloalkyl, and C$_1$-C$_4$ polyhaloalkyl. In a still further aspect, Cy$^4$, when present, is an unsubstituted C$_2$-C$_6$ heterocycloalkyl comprising at least one oxygen or nitrogen atom.

In a further aspect, Cy$^4$, when present, is a C$_2$-C$_5$ heterocycloalkyl comprising at least one oxygen or nitrogen atom, and wherein Cy$^4$ is substituted with 0, 1, 2, or 3 groups independently selected from halogen, C$_1$-C$_4$ alkyl, C$_1$-C$_4$ monohaloalkyl, and C$_1$-C$_4$ polyhaloalkyl. In a still further aspect, Cy$^4$, when present, is a C$_2$-C$_5$ heterocycloalkyl comprising at least one oxygen or nitrogen atom, and wherein Cy$^4$ is substituted with 0, 1, or 2 groups independently selected from halogen, C$_1$-C$_4$ alkyl, C$_1$-C$_4$ monohaloalkyl, and C$_1$-C$_4$ polyhaloalkyl. In yet a further aspect, Cy$^4$, when present, is a C$_2$-C$_5$ heterocycloalkyl comprising at least one oxygen or nitrogen atom, and wherein Cy$^4$ is substituted with 0 or 1 group selected from halogen, C$_1$-C$_4$ alkyl, C$_1$-C$_4$ monohaloalkyl, and C$_1$-C$_4$ polyhaloalkyl. In an even further aspect, Cy$^4$, when present, is a C$_2$-C$_5$ heterocycloalkyl comprising at least one oxygen or nitrogen atom, and wherein Cy$^4$ is monosubstituted with a group selected from halogen, C$_1$-C$_4$ alkyl, C$_1$-C$_4$ monohaloalkyl, and C$_1$-C$_4$ polyhaloalkyl. In a still further aspect, Cy$^4$, when present, is an unsubstituted C$_2$-C$_5$ heterocycloalkyl comprising at least one oxygen or nitrogen atom.

In a further aspect, Cy$^4$, when present, is a C$_2$-C$_4$ heterocycloalkyl comprising at least one oxygen or nitrogen atom, and wherein Cy$^4$ is substituted with 0, 1, 2, or 3 groups independently selected from halogen, C$_1$-C$_4$ alkyl, C$_1$-C$_4$ monohaloalkyl, and C$_1$-C$_4$ polyhaloalkyl. In a still further aspect, Cy$^4$, when present, is a C$_2$-C$_4$ heterocycloalkyl comprising at least one oxygen or nitrogen atom, and wherein Cy$^4$ is substituted with 0, 1, or 2 groups independently selected from halogen, C$_1$-C$_4$ alkyl, C$_1$-C$_4$ monohaloalkyl, and C$_1$-C$_4$ polyhaloalkyl. In yet a further aspect, Cy$^4$, when present, is a C$_2$-C$_4$ heterocycloalkyl comprising at least one oxygen or nitrogen atom, and wherein Cy$^4$ is substituted with 0 or 1 group selected from halogen, C$_1$-C$_4$ alkyl, C$_1$-C$_4$ monohaloalkyl, and C$_1$-C$_4$ polyhaloalkyl. In an even further aspect, Cy$^4$, when present, is a C$_2$-C$_4$ heterocycloalkyl comprising at least one oxygen or nitrogen atom, and wherein Cy$^4$ is monosubstituted with a group selected from halogen, C$_1$-C$_4$ alkyl, C$_1$-C$_4$ monohaloalkyl, and C$_1$-C$_4$ polyhaloalkyl. In a still further aspect, Cy$^4$, when present, is an unsubstituted C$_2$-C$_4$ heterocycloalkyl comprising at least one oxygen or nitrogen atom.

In a further aspect, Cy$^4$, when present, is a C$_4$ heterocycloalkyl comprising at least one oxygen or nitrogen atom, and wherein Cy$^4$ is substituted with 0, 1, 2, or 3 groups independently selected from halogen, C$_1$-C$_4$ alkyl, C$_1$-C$_4$ monohaloalkyl, and C$_1$-C$_4$ polyhaloalkyl. In a still further aspect, Cy$^4$, when present, is a C$_4$ heterocycloalkyl comprising at least one oxygen or nitrogen atom, and wherein Cy$^4$ is substituted with 0, 1, or 2 groups independently selected from halogen, C$_1$-C$_4$ alkyl, C$_1$-C$_4$ monohaloalkyl, and C$_1$-C$_4$ polyhaloalkyl. In yet a further aspect, Cy$^4$, when present, is a C$_4$ heterocycloalkyl comprising at least one oxygen or nitrogen atom, and wherein Cy$^4$ is substituted with 0 or 1 group selected from halogen, C$_1$-C$_4$ alkyl, C$_1$-C$_4$ monohaloalkyl, and C$_1$-C$_4$ polyhaloalkyl. In an even further aspect, Cy$^4$, when present, is a C$_4$ heterocycloalkyl comprising at least one oxygen or nitrogen atom, and wherein Cy$^4$ is monosubstituted with a group selected from halogen, C$_1$-C$_4$ alkyl, C$_1$-C$_4$ monohaloalkyl, and C$_1$-C$_4$ polyhaloalkyl. In a still further aspect, Cy$^4$, when present, is an unsubstituted C$_4$ heterocycloalkyl comprising at least one oxygen or nitrogen atom.

In a further aspect, Cy$^4$, when present, is pyrrolidinyl substituted with 0, 1, 2, or 3 groups independently selected from halogen, C$_1$-C$_4$ alkyl, C$_1$-C$_4$ monohaloalkyl, and C$_1$-C$_4$ polyhaloalkyl. In a still further aspect, Cy$^4$, when present, is pyrrolidinyl substituted with 0, 1, or 2 groups independently selected from halogen, C$_1$-C$_4$ alkyl, C$_1$-C$_4$ monohaloalkyl, and C$_1$-C$_4$ polyhaloalkyl. In yet a further aspect, Cy$^4$, when present, is pyrrolidinyl substituted with 0 or 1 group selected from halogen, C$_1$-C$_4$ alkyl, C$_1$-C$_4$ monohaloalkyl, and C$_1$-C$_4$ polyhaloalkyl. In an even further aspect, Cy$^4$, when present, is pyrrolidinyl monosubstituted with a group selected from halogen, C$_1$-C$_4$ alkyl, C$_1$-C$_4$ monohaloalkyl, and C$_1$-C$_4$ polyhaloalkyl. In a still further aspect, Cy$^4$, when present, is an unsubstituted pyrrolidinyl.

In a further aspect, $Cy^4$, when present, is pyrrolidinyl substituted with 0, 1, 2, or 3 groups independently selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a still further aspect, $Cy^4$, when present, is pyrrolidinyl substituted with 0, 1, or 2 groups independently selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $Cy^4$, when present, is pyrrolidinyl substituted with 0 or 1 group selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In an even further aspect, $Cy^4$, when present, is pyrrolidinyl monosubstituted with a group selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$.

In a further aspect, $Cy^4$, when present, is pyrrolidinyl substituted with 0, 1, 2, or 3 groups independently selected from —F, —Cl, methyl, —$CH_2F$, —$CH_2Cl$, —$CHF_2$, —$CF_3$, —$CHCl_2$, and —$CCl_3$. In a still further aspect, $Cy^4$, when present, is pyrrolidinyl substituted with 0, 1, or 2 groups independently selected from —F, —Cl, methyl, —$CH_2F$, —$CH_2Cl$, —$CHF_2$, —$CF_3$, —$CHCl_2$, and —$CCl_3$. In yet a further aspect, $Cy^4$, when present, is pyrrolidinyl substituted with 0 or 1 group selected from —F, —Cl, methyl, —$CH_2F$, —$CH_2Cl$, —$CHF_2$, —$CF_3$, —$CHCl_2$, and —$CCl_3$. In an even further aspect, $Cy^4$, when present, is pyrrolidinyl monosubstituted with a group selected from —F, —Cl, methyl, —$CH_2F$, —$CH_2Cl$, —$CHF_2$, —$CF_3$, —$CHCl_2$, and —$CCl_3$.

In a further aspect, $Cy^4$, when present, is pyrrolidinyl substituted with 0, 1, 2, or 3 groups independently selected from —F, methyl, —$CH_2F$, —$CHF_2$, and —$CF_3$. In a still further aspect, $Cy^4$, when present, is pyrrolidinyl substituted with 0, 1, or 2 groups independently selected from —F, methyl, —$CH_2F$, —$CHF_2$, and —$CF_3$. In yet a further aspect, $Cy^4$, when present, is pyrrolidinyl substituted with 0 or 1 group selected from —F, methyl, —$CH_2F$, —$CHF_2$, and —$CF_3$. In an even further aspect, $Cy^4$, when present, is pyrrolidinyl monosubstituted with a group selected from —F, methyl, —$CH_2F$, —$CHF_2$, and —$CF_3$.

In one aspect, $Ar^1$ is selected from $C_5$-$C_7$ cycloalkyl, or $C_5$-$C_7$ cycloalkenyl, and wherein $Ar^1$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, —$NHCOR^{20}$, —$NHSO_2R^{20}$, —$CONR^{21a}R^{21b}$, —$SO_2NR^{21a}R^{21b}$, —$CO_2H$, and tetrazole. In further examples, Ar1 is selected from cyclopentyl, cyclohexyl, or cycloheptyl. In a specific example, $Ar^1$ is cyclohexyl. In other examples, $Ar^1$ is selected from cyclopentenyl, cyclohexenyl, cycloheptenyl. In a specific example, $Ar^1$ is cyclohexenyl. In a still further aspect, $Ar^1$ is substituted with 0 or 1 group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In yet a further aspect, $Ar^1$ is monosubstituted with a group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In an even further aspect, $Ar^1$ is unsubstituted.

In a further aspect, $Ar^1$ is cyclohexyl, and wherein $Ar^1$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^1$ is cyclohexyl, and wherein $Ar^1$ is substituted with 0, 1, or 2 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In yet a further aspect, $Ar^1$ is cyclohexyl, and wherein $Ar^1$ is substituted with 0 or 1 group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In an even further aspect, $Ar^1$ is cyclohexyl, and wherein $Ar^1$ is monosubstituted with a group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^1$ is cyclohexyl, and wherein $Ar^1$ is unsubstituted.

In a further aspect, $Ar^1$ is cyclohexenyl, and wherein $Ar^1$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^1$ is cyclohexenyl, and wherein $Ar^1$ is substituted with 0, 1, or 2 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In yet a further aspect, $Ar^1$ is cyclohexenyl, and wherein $Ar^1$ is substituted with 0 or 1 group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In an even further aspect, $Ar^1$ is cyclohexenyl, and wherein $Ar^1$ is monosubstituted with a group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^1$ is cyclohexenyl, and wherein $Ar^1$ is unsubstituted.

In a further aspect, $Ar^1$ is selected from phenyl and pyridinyl, and wherein $Ar^1$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^1$ is selected from phenyl and pyridinyl, and wherein $Ar^1$ is substituted with 0, 1, or 2 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In yet a further aspect, $Ar^1$ is selected from phenyl and pyridinyl, and wherein $Ar^1$ is substituted with 0 or 1 group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In an even further aspect, $Ar^1$ is selected from phenyl and pyridinyl, and wherein $Ar^1$ is monosubstituted with a group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^1$ is selected from phenyl and pyridinyl, and wherein $Ar^1$ is unsubstituted.

In a further aspect, $Ar^1$ is phenyl substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^1$ is phenyl substituted with 0, 1, or 2 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In yet a further aspect, $Ar^1$ is phenyl substituted with 0 or 1 group selected from halogen, —CN, $C_1$-$C_3$ alkyl $C_1$-$C_3$ monohaloalkyl, $C_1$-$C_3$ polyhaloalkyl, cyclopropyl, and —$CO_2H$. In an even further aspect, $Ar^1$ is phenyl monosubstituted with a group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^1$ is unsubstituted phenyl.

In a further aspect, $Ar^1$ is pyridinyl substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^1$ is pyridinyl substituted with 0, 1, or 2 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In yet a further aspect, $Ar^1$ is pyridinyl substituted with 0 or 1 group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In an even further aspect, $Ar^1$ is pyridinyl monosubstituted with a group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^1$ is unsubstituted pyridinyl.

In a further aspect, $Ar^1$ is selected from phenyl and pyridinyl, and wherein $Ar^1$ is substituted with 0, 1, 2, or 3 groups independently selected from halogen, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$ and —$CO_2H$. In a still further aspect, $Ar^1$ is selected from phenyl and pyridinyl, and wherein $Ar^1$ is substituted with 0, 1, or 2 groups independently selected from halogen, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$ and —$CO_2H$. In yet a further aspect, $Ar^1$ is selected from phenyl and pyridinyl, and wherein $Ar^1$ is substituted with 0 or 1 group selected from halogen, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$ and —$CO_2H$. In an even further aspect, $Ar^1$ is selected from phenyl and pyridinyl, and wherein $Ar^1$ is monosubstituted with a group selected from halogen, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$ and —$CO_2H$.

In a further aspect, $Ar^1$ is phenyl substituted with 0, 1, 2, or 3 groups independently selected from halogen, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$ and —$CO_2H$. In a still further aspect, $Ar^1$ is phenyl substituted with 0, 1, or 2 groups independently selected from halogen, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$ and —$CO_2H$. In yet a further aspect, $Ar^1$ is phenyl substituted with 0 or 1 group selected from halogen, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$ and —$CO_2H$. In an even further aspect, $Ar^1$ is phenyl monosubstituted with a group selected from halogen, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$ and —$CO_2H$.

In a further aspect, $Ar^1$ is pyridinyl substituted with 0, 1, 2, or 3 groups independently selected from halogen, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$ and —$CO_2H$. In a still further aspect, $Ar^1$ is pyridinyl substituted with 0, 1, or 2 groups independently selected from halogen, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$ and —$CO_2H$. In yet a further aspect, $Ar^1$ is pyridinyl substituted with 0 or 1 group selected from halogen, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$ and —$CO_2H$. In an even further aspect, $Ar^1$ is pyridinyl monosubstituted with a group selected from halogen, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$ and —$CO_2H$.

In one aspect, $Ar^2$ is selected from aryl and heteroaryl, and wherein $Ar^2$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a further aspect, $Ar^2$ is selected from aryl and heteroaryl, and wherein $Ar^2$ is substituted with 0, 1, or 2 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^2$ is selected from aryl and heteroaryl, and wherein $Ar^2$ is substituted with 0 or 1 group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In yet a further aspect, $Ar^2$ is selected from aryl and heteroaryl, and wherein $Ar^2$ is monosubstituted with a group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In an even further aspect, $Ar^2$ is selected from aryl and heteroaryl, and wherein $Ar^2$ is unsubstituted.

In a further aspect, $Ar^2$ is selected from phenyl, naphthyl, pyridinyl, pyrimidinyl, pyridazinyl, and pyrazinyl, and wherein $Ar^2$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^2$ is selected from phenyl, naphthyl, pyridinyl, pyrimidinyl, pyridazinyl, and pyrazinyl, and wherein $Ar^2$ is substituted with 0, 1, or 2 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In yet a further aspect, $Ar^2$ is selected from phenyl, naphthyl, pyridinyl, pyrimidinyl, pyridazinyl, and pyrazinyl, and wherein $Ar^2$ is substituted with 0 or 1 group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In an even further aspect, $Ar^2$ is selected from phenyl, naphthyl, pyridinyl, pyrimidinyl, pyridazinyl, and pyrazinyl, and wherein $Ar^2$ is monosubstituted with a group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^2$ is selected from phenyl, naphthyl, pyridinyl, pyrimidinyl, pyridazinyl, and pyrazinyl, and wherein $Ar^2$ is unsubstituted.

In a further aspect, $Ar^2$ is selected from phenyl and pyridinyl, and wherein $Ar^2$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In a still further aspect, $Ar^2$ is selected from phenyl and pyridinyl, and wherein $Ar^2$ is substituted with 0, 1, or 2 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In yet a further aspect, $Ar^2$ is selected from phenyl and pyridinyl, and wherein $Ar^2$ is substituted with 0 or 1 group selected from halogen, —CN, $C_1$-$C_3$ alkyl, $C_1$-$C_3$ monohaloalkyl, $C_1$-$C_3$ polyhaloalkyl, cyclopropyl, and —$CO_2H$. In an even further aspect, $Ar^2$ is selected from phenyl and pyridinyl, and wherein $Ar^2$ is monosubstituted with a group selected from halogen, —CN, $C_1$-$C_3$ alkyl, $C_1$-$C_3$ monohaloalkyl, $C_1$-$C_3$ polyhaloalkyl, cyclopropyl, and —CO$_2$H. In a still further aspect, Ar$^2$ is selected from phenyl and pyridinyl, and wherein Ar$^2$ is unsubstituted.

In a further aspect, Ar$^2$ is phenyl substituted with 0, 1, 2, or 3 groups independently selected from halogen, —CN, C$_1$-C$_3$ alkyl, C$_1$-C$_3$ monohaloalkyl, C$_1$-C$_3$ polyhaloalkyl, cyclopropyl, and —CO$_2$H. In a still further aspect, Ar$^2$ is phenyl substituted with 0, 1, or 2 groups independently selected from halogen, —CN, C$_1$-C$_3$ alkyl, C$_1$-C$_3$ monohaloalkyl, C$_1$-C$_3$ polyhaloalkyl, cyclopropyl, and —CO$_2$H. In yet a further aspect, Ar$^2$ is phenyl substituted with 0 or 1 group selected from halogen, —CN, C$_1$-C$_3$ alkyl, C$_1$-C$_3$ monohaloalkyl, C$_1$-C$_3$ polyhaloalkyl, cyclopropyl, and —CO$_2$H. In an even further aspect, Ar$^2$ is phenyl monosubstituted with a group selected from halogen, —CN, C$_1$-C$_3$ alkyl, C$_1$-C$_3$ monohaloalkyl, C$_1$-C$_3$ polyhaloalkyl, cyclopropyl, and —CO$_2$H. In a still further aspect, Ar$^2$ is unsubstituted phenyl.

In a further aspect, Ar$^2$ is pyridinyl substituted with 0, 1, 2, or 3 groups independently selected from halogen, —CN, C$_1$-C$_3$ alkyl, C$_1$-C$_3$ monohaloalkyl, C$_1$-C$_3$ polyhaloalkyl, cyclopropyl, and —CO$_2$H. In a still further aspect, Ar$^2$ is pyridinyl substituted with 0, 1, or 2 groups independently selected from halogen, —CN, C$_1$-C$_3$ alkyl, C$_1$-C$_3$ monohaloalkyl, C$_1$-C$_3$ polyhaloalkyl, cyclopropyl, and —CO$_2$H. In yet a further aspect, Ar$^2$ is pyridinyl substituted with 0 or 1 group selected from halogen, —CN, C$_1$-C$_3$ alkyl, C$_1$-C$_3$ monohaloalkyl, C$_1$-C$_3$ polyhaloalkyl, cyclopropyl, and —CO$_2$H. In an even further aspect, Ar$^2$ is pyridinyl monosubstituted with a group selected from halogen, —CN, C$_1$-C$_3$ alkyl, C$_1$-C$_3$ monohaloalkyl, C$_1$-C$_3$ polyhaloalkyl, cyclopropyl, and —CO$_2$H. In a still further aspect, Ar$^2$ is unsubstituted pyridinyl.

In a further aspect, Ar$^2$ is selected from phenyl and pyridinyl, and wherein Ar$^2$ is substituted with 0, 1, 2, or 3 groups independently selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$ and —CO$_2$H. In a still further aspect, Ar$^2$ is selected from phenyl and pyridinyl, and wherein Ar$^2$ is substituted with 0, 1, or 2 groups independently selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$ and —CO$_2$H. In yet a further aspect, Ar$^2$ is selected from phenyl and pyridinyl, and wherein Ar$^2$ is substituted with 0 or 1 group selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_3$, —CCl$_3$, —CH$_2$CHF$_2$, —CH$_2$CF$_3$, —CH$_2$CHCl$_2$, —CH$_2$CCl$_3$ and —CO$_2$H. In an even further aspect, Ar$^2$ is selected from phenyl and pyridinyl, and wherein Ar$^2$ is monosubstituted with a group selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$ and —CO$_2$H.

In a further aspect, Ar$^2$ is phenyl substituted with 0, 1, 2, or 3 groups independently selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$ and —CO$_2$H. In a still further aspect, Ar$^2$ is phenyl substituted with 0, 1, or 2 groups independently selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$ and —CO$_2$H. In yet a further aspect, Ar$^2$ is phenyl substituted with 0 or 1 group selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$ and —CO$_2$H. In an even further aspect, Ar$^2$ is phenyl monosubstituted with a group selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$ and —CO$_2$H.

In a further aspect, Ar$^2$ is pyridinyl substituted with 0, 1, 2, or 3 groups independently selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$ and —CO$_2$H. In a still further aspect, Ar$^2$ is pyridinyl substituted with 0, 1, or 2 groups independently selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$ and —CO$_2$H. In yet a further aspect, Ar$^2$ is pyridinyl substituted with 0 or 1 group selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$ and —CO$_2$H. In an even further aspect, Ar$^2$ is pyridinyl monosubstituted with a group selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$ and —CO$_2$H.

In specific examples, disclosed herein are compounds having the following structure.

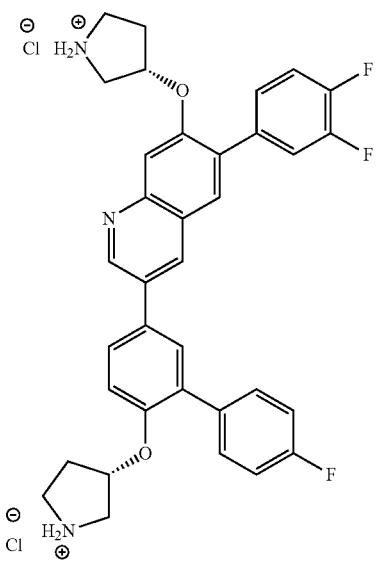

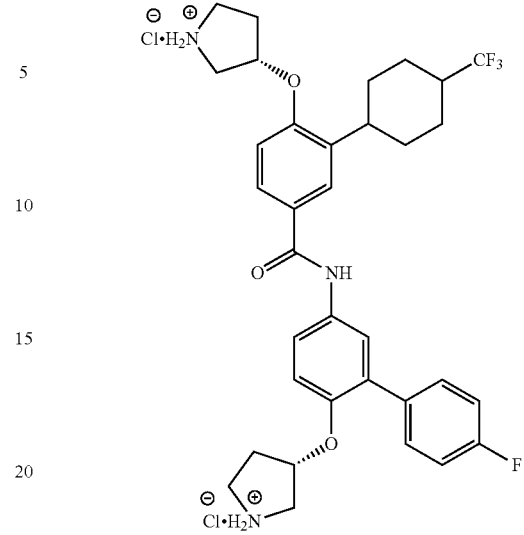

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

In specific examples, the type of cancer is TNBC.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publiation No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Vims (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a vims that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex vims in the treatment of non-small cell lung cancer (Toyoizumi, et al., "Combined therapy with chemotherapeutic agents and herpes simplex virus type IICP34.5 mutant (HSV-1716) in human non-small cell lung cancer," Human Gene Therapy, 1999, 10(18): 17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described in Table 1. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

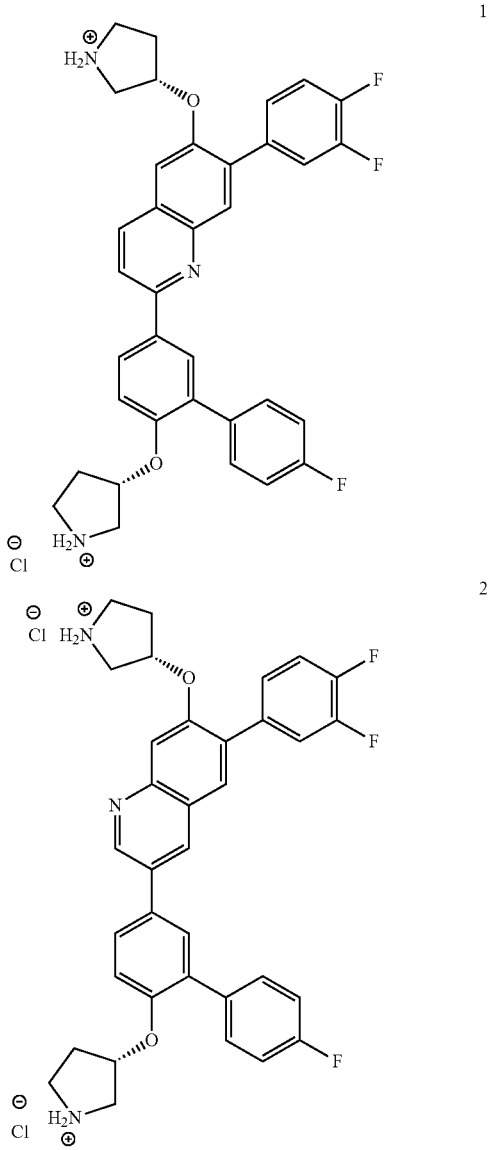

The synthetic routes to prepare 1 and 2 are shown in Schemes 1A-1D. The esterification of 4-bromo-3-hydroxybenzoic acid and then the Mitsunobu reaction with (R)—N-Boc-3-pyrrolidinol offered 4. The Suzuki coupling reaction of 4 with 3,4-difluorophenylboronic acid and then the hydrolysis of the methyl ester of 5 afforded 6. The Curtius rearrangement of 6 and the deprotection of the Cbz protecting group generated 8. The methyl ester group of the key intermediate 10 was reduced to a hydroxymethyl group by DIBAL-H and then the oxidation of the alcohol group to aldehyde resulted in 12. The expoxidation of 12 by trimethylsulfoxonium iodide offered 13. The reaction of intermediate 17 with 12 and acrylic acid produced 18. The deprotection of the Boc protecting group afforded the final product 1. The reaction of 8 with 13 under $FeCl_3$ conditions offered 19. The deprotection of the Boc protecting group provided the final product 2.

Scheme 1A and 5B.
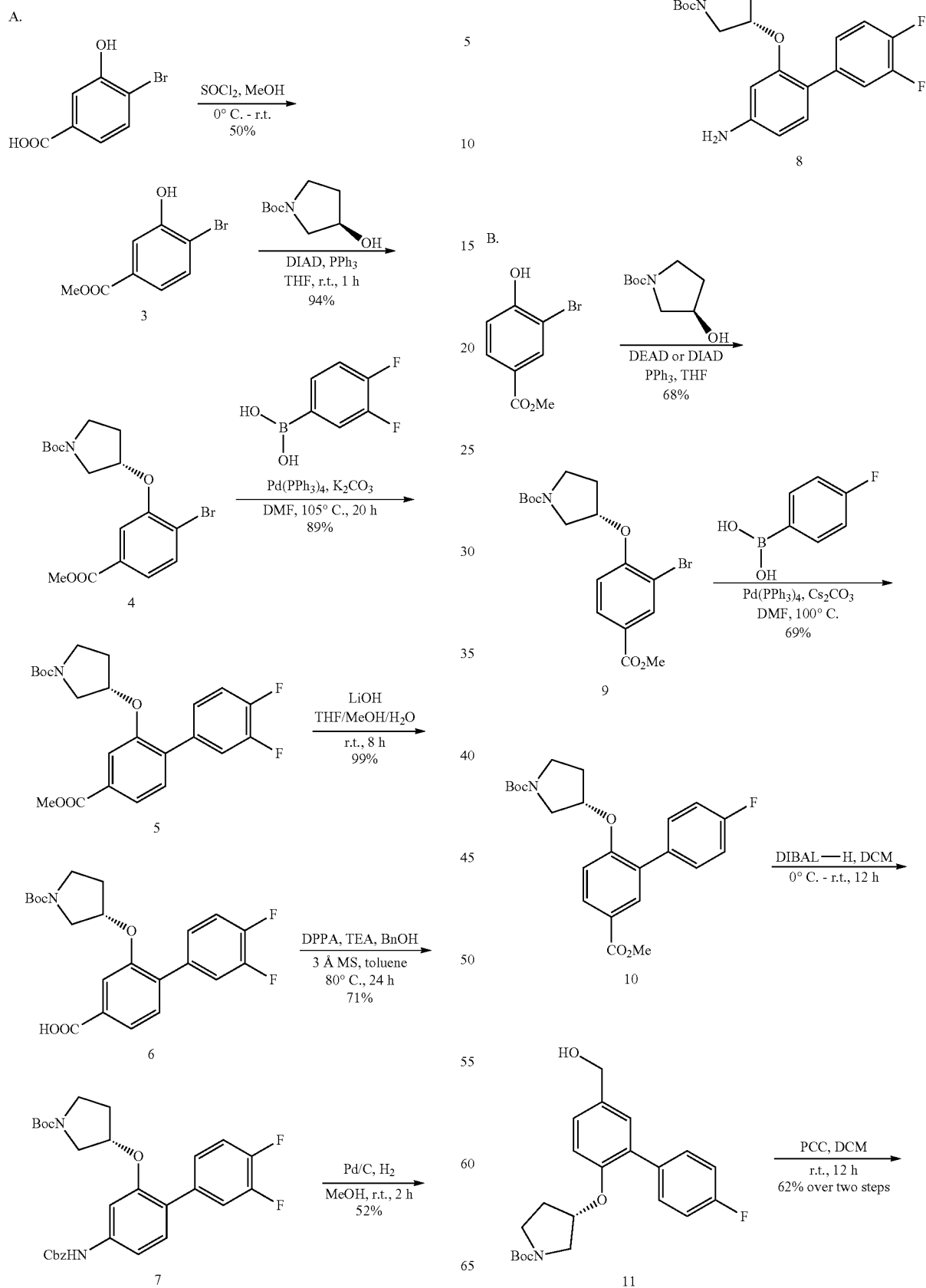

37
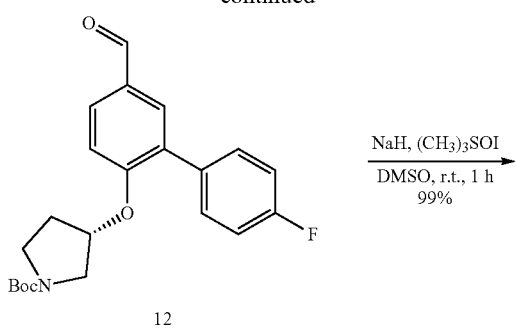
12
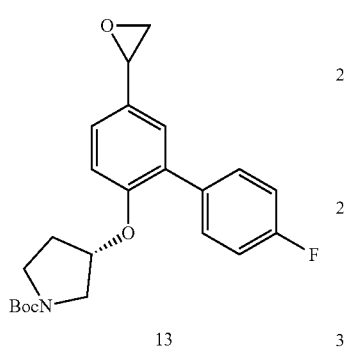
13
C.
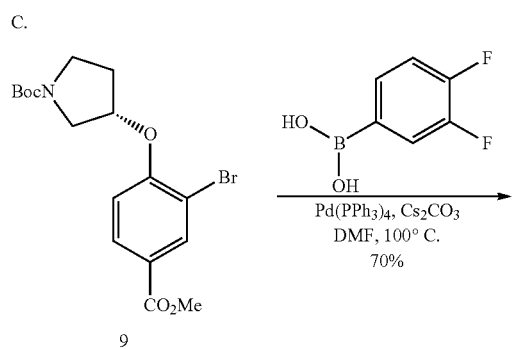
9
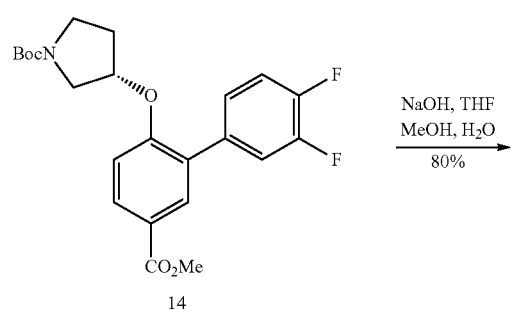
14
38
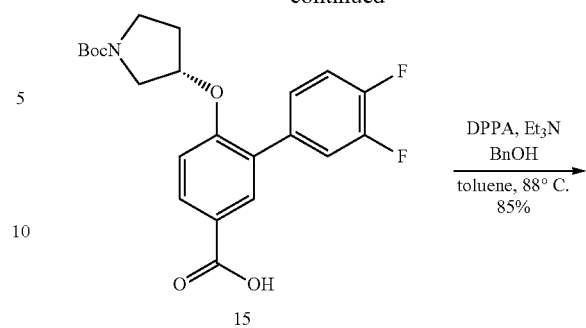
15
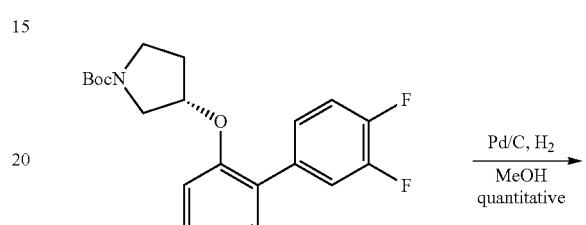
16
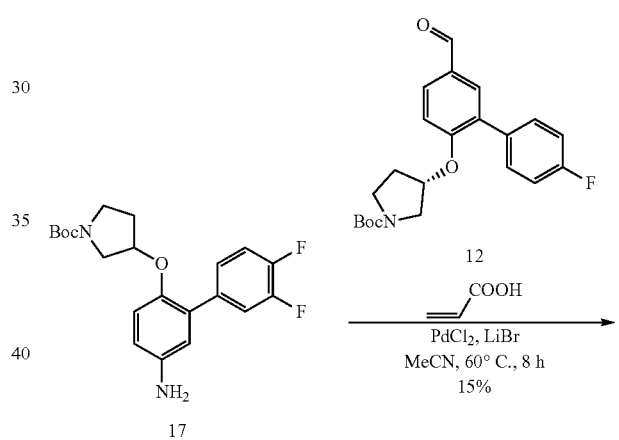
17
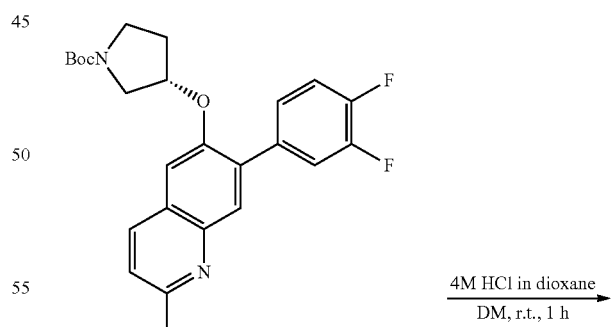
18

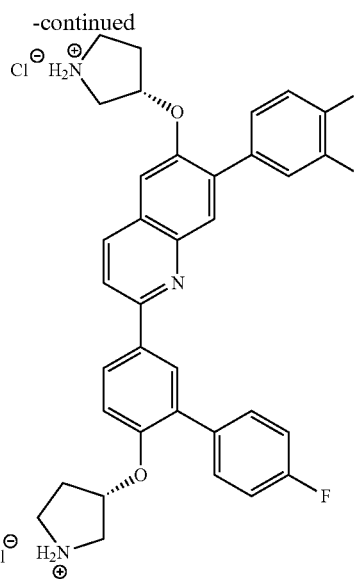

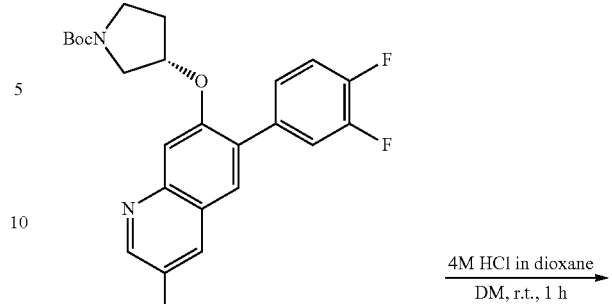

D.

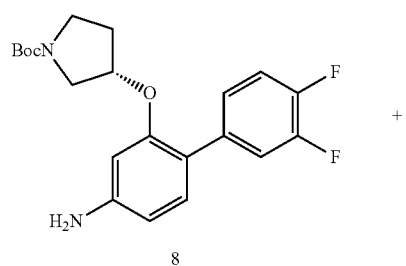

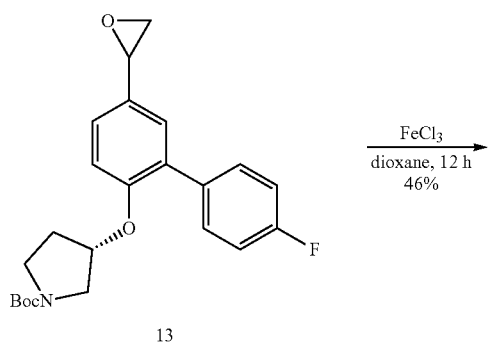

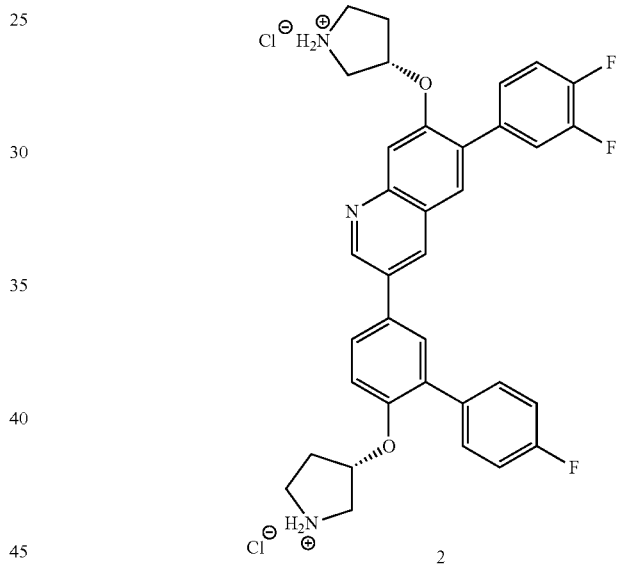

Methyl 4-bromo-3-hydroxybenzoate (3)

To a solution of 4-bromo-3-hydroxybenzoic acid (5.00 g, 13.80 mmol) in MeOH (30 mL) was added SOCl$_2$ (2.50 g, 20.70 mmol) dropwise over 10 min at 0-5° C. The mixture was stirred 3 h at room temperature. The solvent was then removed under reduced pressure, and the residue was taken into EtOAc (150 mL). The solution was washed with aqueous Na$_2$CO$_3$ (50 mL and brine (50 mL×3) and dried over Na$_2$SO$_4$. The inorganic solid was removed by filtrations and the organic solvent removed under reduced pressure to yield 3 (1.61 g, 50%) as a white solid. $^1$H NMR (300 MHz, d$^6$-DMSO): δ ppm 10.74 (s, 1H), 7.62 (d, J=8.1 Hz, 1H), 7.51 (d, J=2.1 Hz, 1H), 7.28 (dd, J=2.1, 8.1 Hz, 1H), 3.81 (s, 3H). $^{13}$C NMR (75 MHz, d$^6$-DMSO): δ ppm 166.33, 154.99, 134.02, 130.70, 121.61, 116.98, 115.77, 52.99.

(S)-tert-butyl 3-(2-bromo-5-(methoxycarbonyl)phenoxy)pyrrolidine-1-carboxylate (4)

To a solution of methyl 3 (0.50 g, 2.16 mmol), (R)-tert-butyl 3-hydroxypyrrolidine-1-carboxylate (0.40 g, 2.16 mmol) and triphenylphosphine (0.68 g, 2.59 mmol) in dry THF (30 mL) was added diisopropyl azodicarboxylate (0.52 g, 2.59 mmol) at 0° C. Then, the temperature was allowed to rise to room temperature and stir for another 1 h. Upon completion, the reaction was diluted with $CH_2Cl_2$ (150 mL), washed with NaOH (1M) (50 mL×2), brine (50 mL×2), dried over $Na_2SO_4$, and concentrated to give the crude product. The crude product was then purified by column chromatography (silica gel, hexanes:acetone=10:1 to 8:1) to yield 4 (0.81 g, 94% yield) as white solid. $^1$H NMR (300 MHz, $CDCl_3$): δ ppm 7.59 (d, J=8.7 Hz, 1H), 7.50 (d, J=9.0 Hz, 2H), 4.99 (s, 1H), 3.89 (s, 3H), 3.63-3.58 (br.s, 4H), 2.24-2.10 (br.m, 2H), 1.44 (s, 9H). $^{13}$C NMR (75 MHz, $CDCl_3$): δ ppm 166.43, 154.73, 153.94, 133.92, 130.64, 123.68, 119.53, 115.40, 79.78, 78.57, 52.63, 51.59, 44.34, 31.93, 31.15, 28.72.

(S)-tert-butyl 3-((3',4'-difluoro-4-(methoxycarbonyl)-[1,1'-biphenyl]-2-yl)oxy)pyrrolidine-1-carboxylate (5)

To a solution of 4 (1 g, 2.50 mmol) in dry DMF (25 mL) under anhydrous condition was added (3,4-difluorophenyl) boronic acid (0.47 g, 3.00 mmol), $Pd(PPh_3)_4$ (0.14 g, 0.13 mmol), and $K_2CO_3$ (0.52 g, 3.75 mmol). The mixture was heated to 105° C. under argon and stirred for 20 h. Then, the reaction mixture was cooled to room temperature, diluted with ethyl acetate, washed with water and brine, dried over $Na_2SO_4$, and concentrated under vacuum. The residue was purified by column chromatography to yield 5 as yellow solid (0.96 g, 89% yield). $^1$H NMR (300 MHz, $CDCl_3$): δ ppm 7.72 (dd, J=1.8 Hz, 7.8 Hz, 1H), 7.59 (s, 1H), 7.36 (d, J=8.1 Hz), 7.34-7.28 (m, 1H), 7.22-7.12 (m, 2H), 5.00-4.97 (m, 1H), 3.94 (s, 3H), 3.62-3.43 (br.m, 3H), 3.39-3.23 (m, 1H), 2.14-2.04 (m, 2H), 1.44 (s, 9H).

(S)-2-((1-(tert-butoxycarbonyl)pyrrolidin-3-yl)oxy)-3',4'-difluoro-[1,1'-biphenyl]-4-carboxylic Acid (6)

To the solution of 5 (0.33 g, 0.75 mmol) in a solvent mixture (14 mL, THF:MeOH:$H_2O$=4:2:1) was added LiOH (0.14 g, 6.00 mmol). The mixture was stirred for 8 h at room temperature. Then, the pH value was adjusted to 4-5 with HCl (1 M), diluted with water (50 mL), and extracted with EtOAc (50 mL×3). The combined organic phase was dried over $Na_2SO_4$ and concentrated under vacuum to afford 6 (0.31 g, 99% yield) as white solid. It was used directly in next step without further purification. $^1$H NMR (300 MHz, $CDCl_3$): δ ppm 7.78 (d, J=7.8 Hz, 1H), 7.64 (s, 1H), 7.39 (d, J=8.1 Hz, 1H), 7.35-7.30 (m, 1H), 7.22-7.17 (m, 2H), 5.01 (s, 1H), 3.76-3.43 (br.m, 3H), 3.41-3.23 (m, 1H), 2.21-2.01 (m, 2H), 1.46 (s, 9H). $^{13}$C NMR (75 MHz, $CDCl_3$): δ ppm 154.92, 153.87, 151.78, 135.31, 134.27, 131.22, 130.23, 125.77, 123.78, 118.83, 118.59, 117.26, 117.03, 115.14, 80.16, 51.40, 44.27, 28.67.

(S)-tert-butyl 3-((4-amino-3',4'-difluoro-[1,1'-biphenyl]-2-yl)oxy)pyrrolidine-1-carboxylate (8)

To a solution of 6 (0.42 g, 1.01 mmol) in dry toluene (20 mL) under anhydrous conditions was added DPPA (0.28 g, 1.01 mmol), $Et_3N$ (0.20 g, 2.02 mmol), benzyl alcohol (1.00 mL), and activated molecular sieves (2 g). The mixture was stirred at room temperature for 10 min and then heated to 80° C. under nitrogen for 24 h. Upon completion the molecule sieves were filtered and the solution diluted with EtOAc (50 mL). The organic layer was washed with water (50 mL), brine (50 mL), dried over $MgSO_4$, solids filtered, and the solvent removed under reduced pressure. The residue was purified by column chromatography to yield 7 (0.38 g, 71%).

To a solution of 7 (0.75 g, 1.42 mmol) in MeOH (20 ml) was added 10% Pd on activated carbon (0.07 g, 10% by weight). The air was evacuated and exchanged with the $H_2$ gas three times. The reaction mixture was allowed to stir under $H_2$ for 2 h and then filter through celite. The solvent was removed under reduced pressure to yield 8 (0.29 g, 52% yield). $^1$H NMR (500 MHz, $CDCl_3$): δ ppm 7.08 (d, J=8.0 Hz, 1H), 6.37 (d, J=8.0 Hz, 1H), 6.25 (s, 1H), 4.79-4.76 (m, 1H), 3.78 (brs, 2H), 3.64-3.25 (m, 4H), 2.22-1.97 (m, 2H), 1.45 (s, 9H).

tert-Butyl (S)-3-(2-bromo-4-(methoxycarbonyl) phenoxy) pyrrolidine-1-carboxylate (9)

To a solution of methyl 3-bromo-4-hydroxybenzoate (7.40 g, 32.04 mmol) in dry THL (100 mL) under anhydrous conditions was added (R)-tert-butyl 3-hydroxypyrrolidine-1-carboxylate (5.00 g, 26.70 mmol), DEAD (6.31 mL, 40.01 mmol), triphenyl phosphine (10.51 g, 40.01 mmol), and stirred for 1 h at room temperature under argon. Upon completion, the reaction was diluted with $CH_2Cl_2$ (100 mL). The organic layer was washed with water (2×50 ml), brine (50 mL), and dried over $MgSO_4$. After the filtration, the solvent removed under reduced pressure. The residue was then purified by column chromatography (silica gel, hexanes:EtOAc=3:1) to yield 9 (7.21 g, 68% yield) as a white solid. $^1$H NMR (500 MHz, $CDCl_3$): δ ppm 8.22 (s, 1H), 7.93 (d, J=8.0 Hz, 1H), 6.85 (d, J=8.0 Hz, 1H), 5.00-4.98 (m, 1H), 3.88 (s, 3H), 3.63-3.56 (m, 4H), 2.23-2.13 (m, 2H), 1.45 (s, 9H). $^{13}$C NMR (125 MHz, $CDCl_3$): δ ppm 186.39, 165.67, 157.47, 143.72, 135.31, 130.41, 124.36, 113.33, 79.76, 79.74, 78.32, 52.29, 51.57, 51.22, 44.25, 43.84, 31.85, 31.02, 28.60. MS (ESI) m/z=400.6 $[M+H]^+$.

tert-Butyl (S)-3-((4'-fluoro-5-(methoxycarbonyl)-[1,1'-biphenyl]-2-yl) oxy) pyrrolidine-1-carboxylate (10)

To a solution of 9 (1.00 g, 2.50 mmol) in dry DMF (25 mL) under anhydrous conditions was added (4-fluorophenyl) boronic acid (0.42 g, 3.00 mmol), $Pd(PPh_3)_4$ (0.14 g, 0.13 mmol), and $Cs_2CO_3$ (1.22 g, 3.75 mmol). The mixture was heated to 80° C. under argon and stirred for 20 h. The solvent was then removed under reduced pressure, and the residue was taken into EtOAc (100 mL). The solution was washed with water (50 mL) and brine (50 mL), and dried over MgSO$_4$. After the filtration, the solvent was removed under reduced pressure. The residue was purified by column chromatography (silica gel, hexanes:EtOAc=1:3) to yield 10 (0.71 g, 69% yield) as a white solid. $^1$H NMR (500 MHz, CDCl$_3$): δ ppm 8.00 (d, J=6.8 Hz, 2H), 7.43 (dd, J=5.6, 8.2 Hz, 2H), 7.08 (t, J=8.5 Hz, 2H), 6.94 (d, J=9.0 Hz, 1H), 4.97-4.95 (m, 1H), 3.90 (s, 3H), 3.66-3.29 (m, 4H), 2.11-2.08 (m, 2H), 1.44 (s, 9H). $^{13}$C NMR (125 MHz, CDCl$_3$): δ ppm 166.76, 163.29, 161.33, 157.67, 154.61, 132.81, 131.17, 131.11, 130.69, 123.46, 115.15, 115.02, 113.14, 112.85, 79.77, 52.16, 51.60, 51.24, 51.23, 51.21, 44.23, 44.21, 44.20, 43.92, 43.89, 31.70, 30.98, 30.97, 28.61. MS (ESI) m/z=416.7 [M+H]$^+$.

(S)-tert-butyl 3-((4'-fluoro-5-formyl-[1,1'-biphenyl]-2-yl)oxy)pyrrolidine-1-carboxylate (12)

To a solution of 10 (1.00 g, 2.41 mmol) in DCM (30 mL) was added DIBAL-H (3.61 mL, 1.0 M in THF) dropwise at −78° C. The temperature was allowed to rise to room temperature and the mixture was stirred overnight. Then the reaction was quenched with NH$_4$Cl (15 mL), extracted with DCM (50 mL×3) and dried over Na$_2$SO$_4$. After removal of the inorganic solid and the solvent, the residue was purified by column chromatography (hexanes:acetone=5:1-3:1) to yield 11 (0.60) as a yellow oil (MS (ESI) m/z=410.2 [M+Na]$^+$).

To the solution of 11 (0.60 g, 1.55 mmol) in DCM (20 mL) was added PCC (1.00 g, 4.65 mmol). The resulting mixture was stirred at room temperature overnight. Then diluted with DCM (80 mL), washed with brine (20 mL×3) and dried over Na$_2$SO$_4$. After removal of the inorganic solid and the solvent, the residue was purified by column chromatography (hexane:acetone=6:1-5:1) to yield 12 (0.58 g, 62% over 2 steps) as a pale yellow oil. $^1$H NMR (300 MHz, CDCl$_3$): δ ppm 9.96 (s, 1H), 7.89-7.85 (m, 2H), 7.45-7.39 (m, 2H), 7.12-7.02 (m, 3H), 5.04-4.99 (m, 1H), 3.70-3.23 (m, 4H), 2.15-2.09 (m, 2H), 1.45 (s, 9H). $^{13}$C NMR (75 MHz, CDCl$_3$): δ ppm 190.97, 164.14, 160.87, 159.03, 154.65, 133.08, 132.77, 131.64, 131.37, 131.26, 131.15, 130.50, 115.42, 115.13, 113.35, 79.92, 51.52, 44.17, 28.68. MS (ESI) m/z=408.2 [M+Na]$^+$.

(3S)-tert-butyl-3-((4'-fluoro-5-(oxiran-2-yl)-[1,1'-biphenyl]-2-yl)oxy)pyrrolidine-1-carboxylate (13)

To a solution of NaH (60%) (0.094 g, 2.34 mmol) in DMSO (15 mL) was added (CH$_3$)$_3$SOI. The resulting mixture was stirred at room temperature for 5 mins. Then the solution of 12 (0.30 g, 0.78 mmol) in DMSO (5 mL) was added slowly. It was stirred for another 1 h, and poured into ice water (50 mL), extracted with EtOAc (30 mL×3), dried over Na$_2$SO$_4$. Removal of the inorganic solid and the solvent yields 13 (0.32 g, >99% yield) as colorless oil. $^1$H NMR (500 MHz, CDCl$_3$): δ ppm 7.43-7.40 (m, 2H), 7.22-7.18 (m, 2H), 7.07-7.04 (m, 2H), 6.92 (d, J=8.0 Hz, 1H), 4.80-4.84 (m, 1H), 3.87-3.84 (m, 1H), 3.60-3.19 (m, 4H), 3.16-3.13 (m, 1H), 2.85-2.80 (m, 1H), 2.07-1.99 (m, 2H), 1.44 (s, 9H).

tert-Butyl (S)-3-((3',4'-difluoro-5-(methoxycarbonyl)-[1,1'-biphenyl]-2-yl) oxy) pyrrolidine-1-carboxylate (14)

To a solution of 9 (1.00 g, 2.50 mmol) in dry DMF (25 mL) under anhydrous conditions was added (4-fluorophenyl) boronic acid (0.42 g, 3.00 mmol), Pd(PPh$_3$)$_4$ (0.14 g, 0.13 mmol), and Cs$_2$CO$_3$ (1.22 g, 3.75 mmol). The mixture was heated to 80° C. under argon and stirred for 20 h. The solvent was then removed under reduced pressure, and the residue was taken into EtOAc (100 mL). The solution was washed with water (50 mL) and brine (50 mL), and dried over MgSO$_4$. After the filtration, the solvent was removed under reduced pressure. The residue was purified by column chromatography (silica gel, hexanes:EtOAc=1:3) to yield 14 (0.76 g, 70% yield) as white solid. $^1$H NMR (500 MHz, CDCl$_3$): δ ppm 7.99 (d, J=9.0 Hz, 2H,), 7.29 (d, J=8.1 Hz, 1H), 7.16 (d, J=3.5 Hz, 2H), 6.94 (d, J=8.4 Hz, 1H), 4.98-4.96 (m, 1H), 3.89 (s, 3H), 3.66-3.31 (m, 4H), 2.11-2.09 (m, 2H), 1.44 (s, 9H). $^{13}$C NMR (125 MHz, CDCl$_3$): δ ppm 166.57, 157.44, 154.66, 150.84, 148.87, 132.64, 131.12, 129.65, 125.62, 125.59, 125.57, 125.54, 123.47, 118.63, 118.58, 118.56, 118.48, 118.45, 118.42, 117.00, 116.97, 116.89, 116.83, 113.01, 112.81, 79.86, 76.47, 52.18, 51.58, 51.12, 44.22, 43.83, 31.69, 30.88, 30.87, 28.53. MS (ESI) m/z=434.6 [M+H]$^+$.

(S)-6-((1-(tert-Butoxycarbonyl) pyrrolidin-3-yl) oxy)-3',4'-difluoro-[1,1'-biphenyl]-3-carboxylic Acid (15)

To a solution of 14 (1.18 g, 2.72 mmol) in a solvent mixture (10 mL, THF:H$_2$O:MeOH=4:1:1) was added 6 M NaOH (15 mL), and the reaction stirred at room temperature for 5 h. THF and MeOH were then removed under reduced pressure. The remaining aqueous solution was acidified with 6 M HCl to pH=4 and extracted with EtOAc (50 mL). The organic layer was washed with water (50 mL), brine (50 mL), and dried over MgSO$_4$. After the filtration, the solvent was removed under reduced pressure to yield 15 (0.91 g, 80%) as white solid. $^1$H NMR (500 MHz, CDCl$_3$): δ ppm 8.10-8.02 (m, 2H), 7.31-7.26 (m, 1H), 7.19-7.16 (m, 2H), 6.97 (d, J=8.7 Hz, 1H), 5.03-5.00 (m, 1H), 3.71-3.33 (m, 4H), 2.16-2.12 (m, 2H), 1.46 (s, 9H). $^{13}$C NMR (125 MHz, d$^6$-DMSO/CDCl$_3$): δ ppm 171.12, 170.88, 158.18, 158.03, 154.96, 154.62, 150.92, 150.90, 148.96, 148.94, 148.93, 148.85, 148.83, 134.23, 133.19, 131.80, 129.74, 129.68, 125.60, 122.73, 118.65, 118.51, 117.00, 116.86, 112.98, 112.81, 80.18, 76.50, 51.63, 51.13, 44.29, 43.87, 31.69, 30.89, 28.55.

tert-Butyl (S)-3-((5-(((benzyloxy) carbonyl) amino)-3',4'-difluoro-[1,1'-biphenyl]-2-yl) oxy) pyrrolidine-1-carboxylate (16)

To a solution of 15 (0.99 g, 2.35 mmol) in dry toluene (30 mL) under anhydrous conditions was added DPPA (5.07 mL, 23.52 mmol), Et$_3$N (3.28 mL, 23.52 mmol), benzyl alcohol (5.00 mL, 0.048 mmol), and activated molecular sieves (2 g). The mixture was stirred at room temperature for 10 min and then heated to 80° C. under nitrogen for 24 h. Upon completion, the molecule sieves were filtered and the solution diluted with EtOAc (50 mL). The organic layer was washed with water (50 mL), brine (50 mL), and dried over MgSO$_4$. After the filtration, the solvent was removed under reduced pressure. The residue was purified by column chromatography (silica gel, hexanes:EtOAc=3:1) to yield 16 (1.05 g, 85% yield) as white solid. $^1$H NMR (500 MHz, CDCl$_3$): δ ppm 7.37-7.26 (m, 9H), 7.13-7.10 (m, 2H), 6.83 (s, 1H), 5.17 (s, 2H), 4.71-4.69 (m, 1H), 3.56-3.19 (m, 4H), 2.02-1.93 (m, 2H), 1.44 (s, 9H). $^{13}$C NMR (125 MHz, CDCl$_3$): δ ppm 154.62, 154.48, 153.91, 150.60, 149.86, 149.67, 148.63, 136.19, 134.82, 132.43, 130.67, 130.47, 128.57, 128.29, 128.24, 127.44, 126.93, 125.48, 121.84, 119.88, 119.87, 119.86, 118.50, 118.38, 118.36, 118.25, 116.78, 116.71, 116.64, 116.57, 115.71, 115.51, 79.59, 79.58, 77.84, 77.07, 66.92, 51.43, 50.95, 44.14, 43.77, 31.45, 30.71, 28.45.

tert-Butyl (S)-3-((5-amino-3',4'-difluoro-[1,1'-biphenyl]-2-yl) oxy) pyrrolidine-1-carboxylate (17)

To a solution of 16 (0.74 g, 1.42 mmol) in MeOH (20 ml) was added 10% Pd on activated carbon (0.07 g, 10% by weight). The air was evacuated and exchanged with the H$_2$ gas three times. The reaction mixture was allowed to stir under H$_2$ for 2 h and then filter through celite. The solvent was removed under reduced pressure to yield 17 (0.55 g, quantitative yield) as off-white solid. $^1$H NMR (500 MHz, CDCl$_3$): δ ppm 7.29-7.26 (m, 1H), 7.15-7.13 (m, 2H), 6.79-6.76 (m, 1H), 6.64-6.60 (m, 2H), 4.59-4.56 (m, 1H), 3.58 (brs, 2H), 3.55-3.14 (m, 4H), 1.89-1.87 (m, 2H), 1.43 (s, 9H). $^{13}$C NMR (125 MHz, CDCl$_3$): δ ppm 154.58, 154.46, 150.78, 150.51, 148.81, 148.43, 146.62, 146.43, 141.53, 135.41, 135.36, 131.67, 125.46, 125.43, 125.41, 125.38, 118.50, 118.35, 118.20, 118.00, 117.89, 117.57, 117.46, 116.80, 116.72, 116.67, 116.58, 116.42, 115.70, 115.58, 79.37, 78.68, 77.90, 51.41, 50.90, 44.16, 43.79, 31.52, 30.80, 28.51. MS (ESI) m/z=391.7 [M+H]$^+$.

(S)-tert-butyl-3-((2-(6-(((S)-1-(tert-butoxycarbonyl)pyrrolidin-3-yl)oxy)-4'-fluoro-[1,1'-biphenyl]-3-yl)-7-(3,4-difluorophenyl)quinolin-6-yl)oxy)pyrrolidine-1-carboxylate (18)

A 25 mL of round bottom flask was charged with a solution of 17 (0.050 g, 0.13 mmol) and 12 (0.049 g, 0.13 mmol) in MeCN (5 mL). Then LiBr (0.011 g, 0.13 mmol), PdCl$_2$ (0.0020 g, 0.013 mmol), acrylic acid (0.019 g, 0.13 mmol) were added under magnetic stirring. The resulting mixture was heated to 60° C. for 8 h, diluted with EtOAc (60 mL), washed with brine (20 mL×3), dried over Na$_2$SO$_4$. After removal of the inorganic solid and the solvent, the residue was purified by column chromatography (hexanes:EtOAc=2:1-1:1) to yield 18 (0.015 g, 15%) as a yellow solid. $^1$H NMR (500 MHz, CDCl$_3$): δ ppm 8.12-8.08 (m, 4H), 7.85 (d, J=8.5 Hz, 1H), 7.52 (dd, 7=5.5, 8.0 Hz, 2H), 7.47-7.40 (m, 1H), 7.32-7.30 (m, 1H), 7.24-7.19 (m, 1H), 7.12-7.06 (m, 4H), 5.06-5.03 (m, 1H), 4.96-4.93 (m, 1H), 3.78-3.23 (m, 8H), 2.23-2.04 (m, 4H), 1.46 (s, 9H), 1.44 (s, 9H). MS (ESI) m/z=782.4 [M+H]$^+$, MS (ESI) m/z=804.4 [M+Na]$^+$.

7-(3,4-difluorophenyl)-2-(4'-fluoro-6-((S)-pyrrolidin-3-yloxy)-[1,1'-biphenyl]-3-yl)-6-((S)-pyrrolidin-3-yloxy)quinoline dihydrochloride (1)

To a solution of 18 (0.078 g, 0.1 mmol) in DCM (2 mL) under anhydrous conditions was added 4 M HCl in dioxane (5 mL) and the mixture was then stirred at room temperature for 1-1.5 h. The solvent was removed under reduced pressure to yield 1 (0.065 g, quantitative) as yellow solid. $^1$H NMR (500 MHz, CD$_3$OD): δ ppm 8.76 (d, J=10.5 Hz, 1H), 8.25 (d, J=8.5 Hz, 1H), 8.22-8.15 (m, 3H), 7.76 (s, 1H), 7.68-7.61 (m, 3H), 7.51-7.46 (m, 1H), 7.45-7.38 (m, 2H), 7.21 (t, J=9.0 Hz, 2H), 5.46 (s, 1H), 5.35 (s, 1H), 3.77-3.71 (m, 1H), 3.68-3.43 (m, 6H), 3.28-3.24 (m, 1H), 2.49-2.29 (m, 4H). $^{13}$C NMR (126 MHz, CD$_3$OD) δ 163.46, 161.50, 156.87, 153.61, 152.91, 151.41, 149.53, 143.38, 138.19, 135.57, 133.16, 132.98, 131.91, 131.42, 131.32, 131.25, 129.79, 128.51, 126.36, 125.73, 123.61, 121.30, 118.64, 118.51, 117.23, 117.10, 114.85, 114.68, 114.48, 108.75, 102.74, 77.09, 76.76, 50.42, 50.21, 44.32, 44.25, 30.77, 30.65. HRMS (ESI) Calcd for C$_{35}$H$_{30}$F$_3$N$_3$O$_2$ (M+H)$^+$ 582.2368, found 582.2345.

(S)-tert-butyl-3-((3-(6-(((S)-1-(tert-butoxycarbonyl)pyrrolidin-3-yl)oxy)-4'-fluoro-[1,1'-biphenyl]-3-yl)-6-(3,4-difluorophenyl)quinolin-7-yl)oxy)pyrrolidine-1-carboxylate (19)

A 25 mL of round bottom flask equipped with a magnetic stirrer bar was charged with 8 (0.020 g, 0.050 mmol), 13 (0.039 g, 0.10 mmol), FeCl$_3$ (0.0024 g, 0.015 mmol), and dioxane (10 mL). The resulting mixture was heated to reflux overnight. After 12 h, the reactions mixture was diluted with EtOAc (60 mL), washed with brine (20 mL×3) and dried over Na$_2$SO$_4$. After the removal of the inorganic solid and the solvent, the residue was purified by column chromatography (DCM:MeOH=80:1-70:1) to yield 19 (0.018 g, 46%) as a yellow solid. $^1$H NMR (500 MHz, d$^6$-Acetone): δ ppm 9.23 (s, 1H), 8.54 (s, 1H), 7.99 (s, 1H), 7.83-7.81 (m, 2H), 7.66-7.64 (m, 2H), 7.59-7.57 (m, 2H), 7.46-7.33 (m, 3H), 7.19 (t, J=8.5 Hz, 2H), 5.37-5.34 (m, 1H), 5.19-5.14 (m, 1H), 3.73-3.78 (m, 8H), 2.38-2.10 (m, 4H), 1.44-1.40 (m, 18H). MS (ESI) m/z=782.4 [M+H]$^+$.

6-(3,4-difluorophenyl)-3-(4'-fluoro-6-((S)-pyrrolidin-3-yloxy)-[1,1'-biphenyl]-3-yl)-7-((S)-pyrrolidin-3-yloxy)quinoline dihydrochloride (2)

To a solution of 19 (0.078 g, 0.1 mmol) in DCM (2 mL) under anhydrous conditions was added 4 M HCl in dioxane (5 mL) and the mixture was then stirred at room temperature for 1-1.5 h. The solvent was removed under reduced pressure to yield 2 (0.065 g, quantitative) as yellow solid. $^1$H NMR (500 MHz, CD$_3$OD): δ ppm 9.41 (s, 1H), 9.12 (brs, 1H), 8.23 (s, 1H), 7.90 (dd, J=2.5, 8.5 Hz, 1H), 7.86 (d, J=2.0 Hz, 1H), 7.68 (s, 1H), 7.67-7.60 (m, 3H), 7.49-7.39 (m, 2H), 7.36 (d, J=8.5 Hz, 1H), 7.20 (t, J=9.0 Hz, 2H), 5.55 (s, 1H), 5.26 (s, 1H), 3.80 (dd, J=5.0 Hz, 13.0 Hz, 1H), 3.69-3.58 (m, 2H), 3.57-3.50 (m, 2H), 3.48-3.42 (m, 1H), 3.38-3.33 (m, 1H), 3.27-3.21 (m, 1H), 2.57-2.40 (m, 2H), 2.31-2.26 (m, 2H). $^{13}$C NMR (500 MHz, CD$_3$OD): 163.35, 161.39, 157.33, 154.25, 144.86, 134.06, 133.70, 133.68, 132.10, 131.20, 131.13, 130.99, 129.83, 127.57, 126.24, 126.21, 126.19, 118.59, 118.44, 117.06, 116.92, 115.16, 114.75, 114.58, 77.27, 76.78, 50.50, 50.21, 44.36, 44.17, 30.67, 30.56. HRMS (ESI) Calcd for C$_{35}$H$_{30}$F$_3$N$_3$O$_2$ (M+H)$^+$ 582.2368, found 582.2348.

Example 2

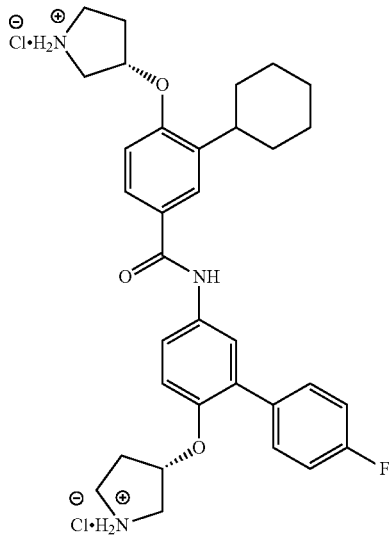

3

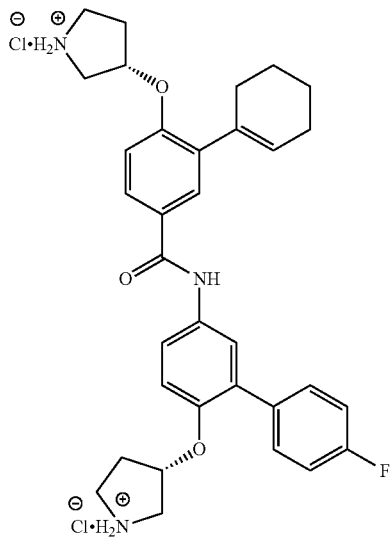

4

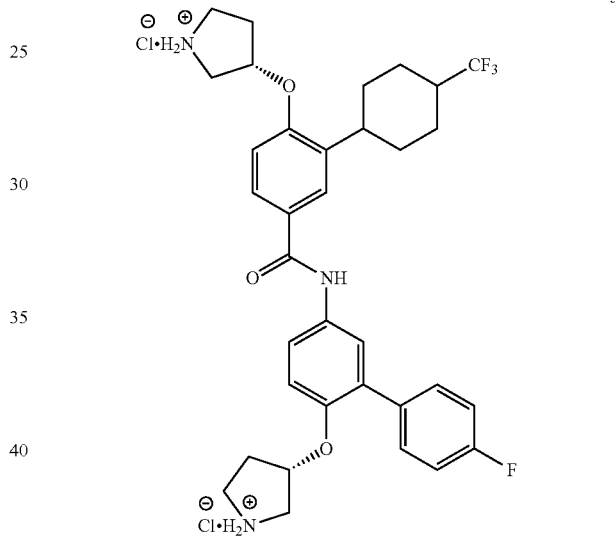

5

The synthetic route for 3-5 is shown in Scheme 2. The Suzuki reaction of 12 with different phenylboronic acids yielded 13. The hydrogenation of the olefin bond in 13 gave 14a-b, respectively, which were then subjected to the Boc deprotection reaction to offer the final products 1 and 3. The direct Boc deprotection reaction of 13 offered 2.

Scheme 2.

A.

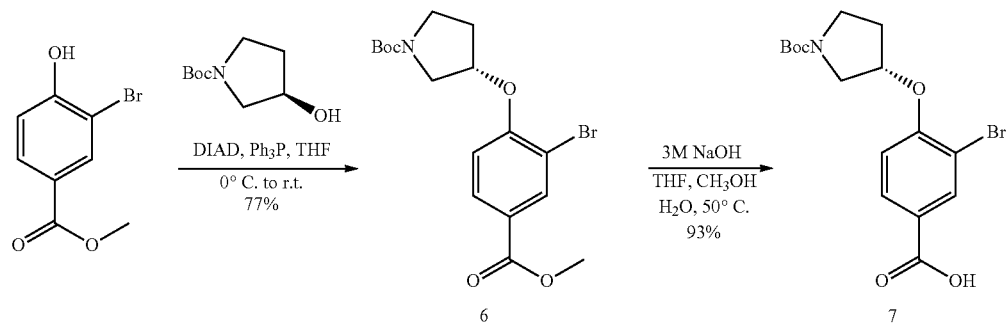

B.
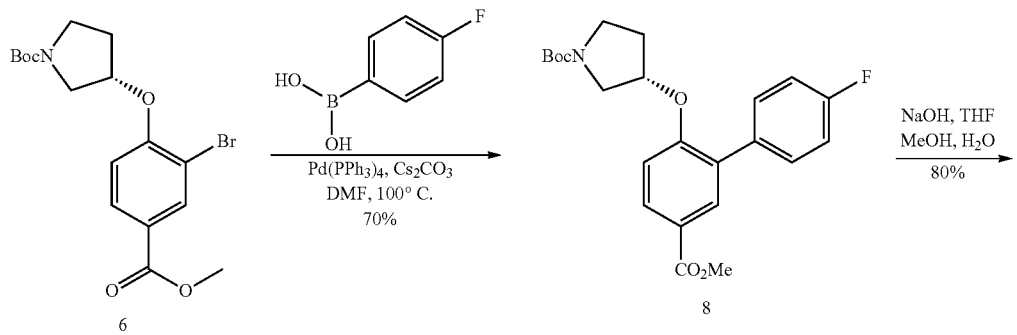
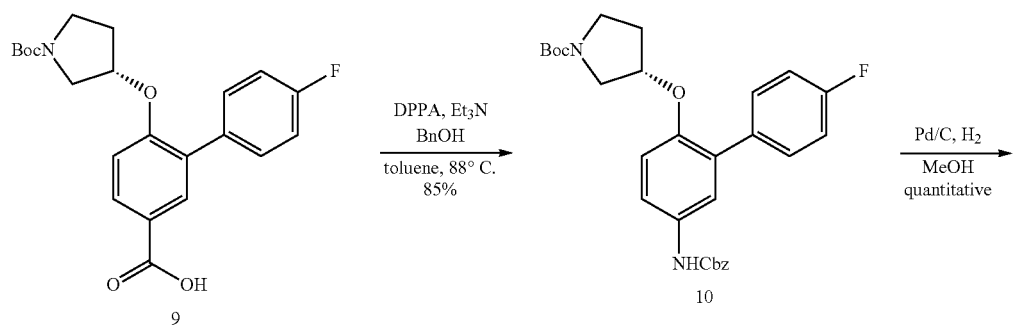
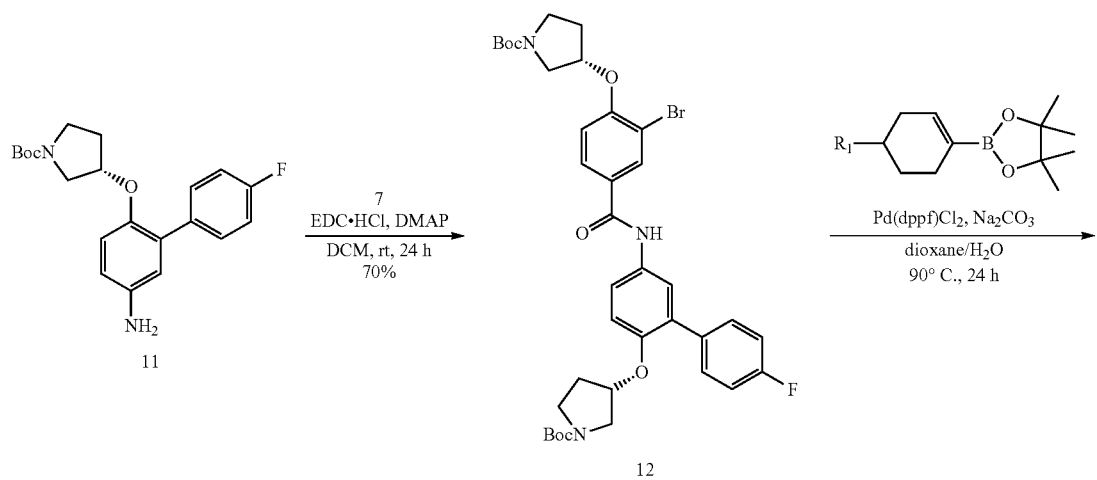

-continued
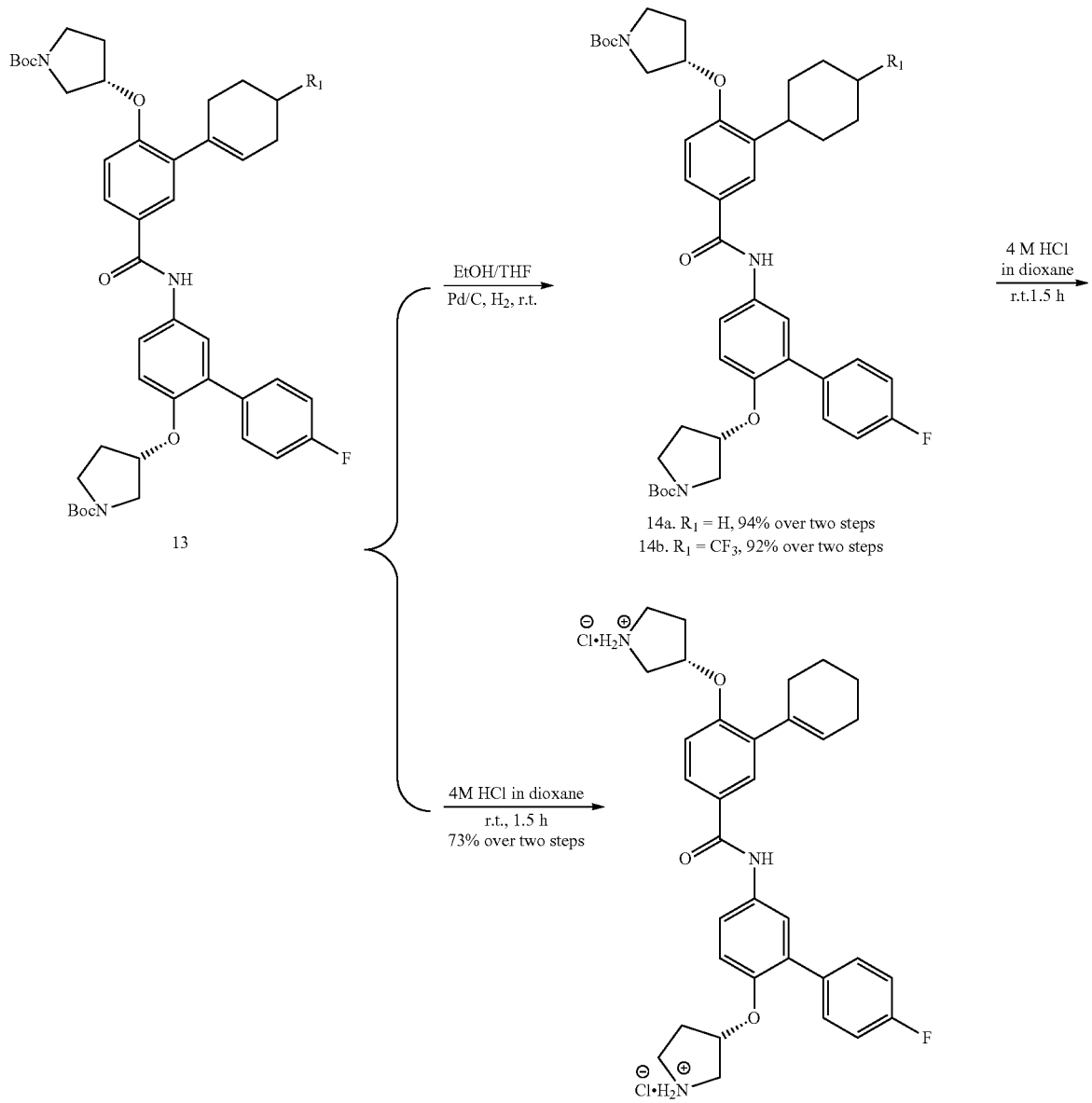

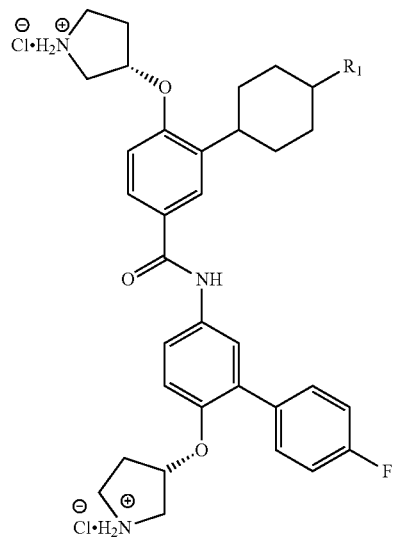

1. $R_1$ = H, 68%
3. $R_1$ = $CF_3$, 62% tert-Butyl (S)-3-(2-bromo-4-(methoxycarbonyl) phenoxy) pyrrolidine-1-carboxylate (6)

To a solution of methyl 3-bromo-4-hydroxybenzoate (0.626 g, 2.70 mmol) in dry THF (35 mL) under anhydrous conditions was added (R)-tert-butyl 3-hydroxypyrrolidine-1-carboxylate (0.505 g, 2.70 mmol) and triphenyl phosphine (1.43 g, 5.39 mmol). The reaction mixture was then cooled in an ice bath, and DIAD (1.12 g, 5.56 mmol) dissolved in THF (10 mL) was added dropwise. The reaction mixture was stirred for 1 h at room temperature under argon. Upon completion the reaction was diluted with ethyl acetate (100 mL). The organic layer was washed with water (2×50 mL), brine (50 mL), dried over $MgSO_4$, solids filtered, and the solvent removed under reduced pressure. The residue was then purified by column chromatography (silica gel, hexanes:EtOAc=5:1) to yield 6 (0.837 g, 77% yield) as white solid. $^1$H NMR (500 MHz, $CDCl_3$): δ ppm 8.22 (s, 1H), 7.93 (d, J=8.0 Hz, 1H), 6.85 (d, J=8.0 Hz, 1H), 5.00-4.98 (m, 1H), 3.88 (s, 3H), 3.63-3.56 (m, 4H), 2.23-2.13 (m, 2H), 1.45 (s, 9H). $^{13}$C NMR (125 MHz, $CDCl_3$): δ ppm 165.67, 157.47, 143.72, 135.31, 130.41, 124.36, 113.33, 79.76, 79.74, 78.32, 52.29, 51.57, 51.22, 44.25, 43.84, 31.85, 31.02, 28.60. MS (ESI) m/z=400.6 $[M+H]^+$.

(S)-3-Bromo-4-((1-(tert-butoxycarbonyl) pyrrolidin-3-yl) oxy) benzoic Acid (7)

To a solution of 6 (1.08 g, 2.70 mmol) in MeOH (10 mL) was added 6 M NaOH (10 mL), and the reaction was allowed to stir at room temperature for 6 h. MeOH was then removed under reduced pressure. The remaining aqueous solution was acidified with 12 M HCl to pH=2. The product was extracted with $CH_2Cl_2$ (50 mL) and the organics washed with water (2×50 mL), brine (50 mL), dried over $MgSO_4$, solids filtered, and solvent removed under reduced pressure to yield 7 (0.97 g, 93% yield) as white solid. $^1$H NMR (300 MHz, $CDCl_3$): δ ppm 8.29 (d, 1H, J=4.7 Hz), 8.01 (t, 1H, J=8.9 Hz), 6.88 (d, 1H, J=8.6 Hz), 5.03-5.01 (m, 1H), 3.70-3.56 (m, 4H), 2.30-2.13 (m, 2H), 1.47 (s, 9H). $^{13}$C NMR (125 MHz, $CDCl_3$): δ ppm 169.84, 157.90, 154.76, 154.49, 135.77, 130.93, 123.49, 113.12, 112.98, 79.94, 78.18, 51.45, 51.07, 44.15, 43.72, 31.67, 30.87, 28.45.

tert-Butyl (S)-3-((4'-fluoro-5-(methoxycarbonyl)-[1,1'-biphenyl]-2-yl) oxy) pyrrolidine-1-carboxylate (8)

To a solution of 6 (1.00 g, 2.50 mmol) in dry DMF (25 mL) under anhydrous conditions was added (4-fluorophenyl) boronic acid (0.42 g, 3.00 mmol), $Pd(PPh_3)_4$ (0.14 g, 0.13 mmol), and $Cs_2CO_3$ (1.22 g, 3.75 mmol). The mixture was heated to 80° C. under argon and stirred for 20 h. The solvent was then removed under reduced pressure, and the residue was taken into EtOAc (100 mL). The solution was washed with water (50 mL) and brine (50 mL), and dried over $MgSO_4$. After the filtration, the solvent was removed under reduced pressure. The residue was purified by column chromatography (silica gel, hexanes:EtOAc=1:3) to yield 8 (0.73 g, 70% yield) as a white solid. $^1$H NMR (500 MHz, $CDCl_3$): δ ppm 8.00 (d, J=6.8 Hz, 2H), 7.43 (dd, J=5.6, 8.2 Hz, 2H), 7.08 (t, J=8.5 Hz, 2H), 6.94 (d, J=9.0 Hz, 1H), 4.97-4.95 (m, 1H), 3.90 (s, 3H), 3.66-3.29 (m, 4H), 2.11-2.08 (m, 2H), 1.44 (s, 9H). $^{13}$C NMR (125 MHz, $CDCl_3$): δ ppm 166.76, 163.29, 161.33, 157.67, 154.61, 132.81, 131.17, 131.11, 130.69, 123.46, 115.15, 115.02, 113.14, 112.85, 79.77, 52.16, 51.60, 51.24, 51.23, 51.21, 44.23, 44.21, 44.20, 43.92, 43.89, 31.70, 30.98, 30.97, 28.61. MS (ESI) m/z=416.7 $[M+H]^+$.

(S)-6-((1-(tert-Butoxycarbonyl) pyrrolidin-3-yl) oxy)-4'-fluoro-[1,1'-biphenyl]-3-carboxylic Acid (9)

To a solution of 8 (1.13 g, 2.72 mmol) in a solvent mixture (10 mL, THF:$H_2O$:MeOH=4:1:1) was added 6 M NaOH (15 mL), and the reaction stirred at room temperature for 5 h. THF and MeOH were then removed under reduced pressure. The remaining aqueous solution was acidified with 6 M HCl to pH=4 and extracted with EtOAc (50 mL). The organic layer was washed with water (50 mL), brine (50 mL), and dried over $MgSO_4$. After the filtration, the solvent was removed under reduced pressure to yield 9 (0.87 g, 80%) as a white solid. $^1$H NMR (500 MHz, CDCl$_3$): δ 8.07-8.04 (m, 2H), 7.46-7.42 (m, 2H), 7.09 (t, J=8.3 Hz, 2H), 6.97 (d, J=9.5 Hz, 1H), 5.00-4.97 (m, 1H), 3.69-3.30 (m, 4H), 2.14-2.12 (m, 2H), 1.45 (s, 9H). $^{13}$C NMR (125 MHz, CDCl$_3$): δ 171.39, 171.24, 163.33, 161.35, 158.29, 158.22, 154.83, 154.62, 133.41, 133.32, 131.38, 131.17, 131.14, 130.93, 130.87, 122.65, 115.23, 115.09, 114.92, 113.09, 112.75, 79.98, 77.26, 76.48, 51.63, 51.19, 44.26, 43.91, 31.67, 30.92, 28.59.

tert-Butyl (S)-3-((5-(((benzyloxy) carbonyl) amino)-4'-fluoro-[1,1'-biphenyl]-2-yl) oxy) pyrrolidine-1-carboxylate (10)

To a solution of 9 (0.94 g, 2.35 mmol) in dry toluene (30 mL) under anhydrous conditions was added DPPA (5.07 mL, 23.52 mmol), Et$_3$N (3.28 mL, 23.52 mmol), benzyl alcohol (5.00 mL, 0.048 mmol), and activated molecular sieves (2 g). The mixture was stirred at room temperature for 10 min and then heated to 80° C. under nitrogen for 24 h. Upon completion, the molecule sieves were filtered and the solution diluted with EtOAc (50 mL). The organic layer was washed with water (50 mL), brine (50 mL), and dried over MgSO$_4$. After the filtration, the solvent was removed under reduced pressure. The residue was purified by column chromatography (silica gel, hexanes:EtOAc=3:1) to yield 10 (1.01 g, 85% yield) as a white solid. $^1$H NMR (500 MHz, CDCl$_3$): δ ppm 7.43-7.26 (m, 9H), 7.04 (t, J=8.0 Hz, 2H), 6.88 (d, J=8.2 Hz, 1H), 6.73 (brs, 1H), 5.19 (s, 2H), 4.72-4.70 (m, 1H), 3.58-3.17 (m, 4H), 2.02-1.93 (m, 2H), 1.43 (s, 9H). $^{13}$C NMR (125 MHz, CDCl$_3$): δ ppm 162.93, 160.97, 154.52, 153.93, 149.80, 136.21, 133.81, 132.55, 132.47, 131.89, 131.62, 130.92, 128.45, 128.13, 122.01, 121.81, 119.36, 116.08, 115.59, 114.86, 114.74, 114.69, 114.57, 79.46, 79.35, 77.69, 66.73, 51.37, 50.97, 44.03, 43.75, 31.28, 30.60, 28.40. MS (ESI) m/z=507.7 [M+H]$^+$.

tert-Butyl (S)-3-((5-amino-4'-fluoro-[1,1'-biphenyl]-2-yl) oxy) pyrrolidine-1-carboxylate (11)

To a solution of 10 (0.68 g, 1.42 mmol) in MeOH (20 ml) was added 10% Pd on activated carbon (0.07 g, 10% by weight). The air was evacuated and exchanged with the H$_2$ gas three times. The reaction mixture was allowed to stir under H$_2$ for 2 h and then filter through celite. The solvent was removed under reduced pressure to yield 11 (0.53 g, quantitative yield) as an off-white solid. $^1$H NMR (500 MHz, CDCl$_3$): δ ppm 7.41 (dd, J=5.8 Hz, J=8.0 Hz, 2H), 7.03 (d, J=6.0 Hz, 2H), 6.78 (t, J=8.2 Hz, 1H), 6.65-6.59 (m, 2H), 4.53-4.50 (m, 1H), 3.57 (brs, 2H), 3.44-3.09 (m, 4H), 1.97-1.83 (m, 2H), 1.43 (s, 9H). $^{13}$C NMR (125 MHz, CDCl$_3$): δ ppm 162.93, 160.97, 154.52, 153.93, 149.80, 136.21, 133.81, 132.55, 132.47, 131.89, 131.62, 130.92, 128.45, 128.13, 122.01, 121.81, 119.36, 116.08, 115.59, 114.86, 114.74, 114.69, 114.57, 79.46, 79.35, 77.69, 66.73, 51.37, 50.97, 44.03, 43.75, 31.28, 30.60, 28.40. MS (ESI) m/z=373.7 [M+H]$^+$.

tert-butyl (S)-3-((5-(3-bromo-4-(((S)-1-(tert-butoxycarbonyl) pyrrolidin-3-yl) oxy) benzamido)-4'-fluoro-[1,1'-biphenyl]-2-yl) oxy) pyrrolidine-1-carboxylate (12)

To a solution of 7 (1.0 g, 2.6 mmol) in CH$_2$Cl$_2$ (30 ml) was added 11 (0.97 g, 2.6 mmol), EDC•HCl (0.75 g, 3.9 mmol), and DMAP (0.32 g, 2.6 mmol). The mixture was then stirred at room temperature for 24 h. The reaction mixture was diluted with CH$_2$Cl$_2$ (20 mL), washed with water (30 mL), brine (30 mL), and dried over MgSO$_4$. The solid was filtered, and the solvent was removed under the reduced pressure. The residue was then purified by column chromatography to yield 12 as white solid (1.3 g, 70%) $^1$H NMR (500 MHz, acetone-d$_6$): δ ppm 8.91 (s, 1H), 7.62 (s, 1H), 7.41 (dd, J=3.0, 9.0 Hz, 1H), 7.20 (s, 2H), 6.97-6.87 (m, 2H), 6.64 (d, J=9.0 Hz, 1H), 6.57-6.52 (m, 3H), 4.63 (s, 1H), 4.38 (s, 1H), 3.12-2.73 (m, 8H), 2.70-2.54 (m, 1H), 1.72-1.52 (m, 2H), 0.82 (m, 18H). $^{13}$C NMR (125 MHz, acetone-d$_6$): δ ppm 168.05, 163.53, 163.12, 161.18, 156.50, 154.08, 150.44, 134.78, 133.64, 132.81, 131.41, 131.18, 129.40, 128.75, 123.18, 120.90, 115.52, 114.91, 114.40, 112.48, 78.69, 78.50, 77.85, 77.05, 51.65, 51.54, 51.33, 51.17, 44.21, 43.95, 31.53, 31.37, 30.69, 30.36, 27.99.

tert-butyl (S)-3-((5-(4-(((S)-1-(tert-butoxycarbonyl) pyrrolidin-3-yl) oxy)-3-cyclohexylbenzamido)-4'-fluoro-[1,1'-bi-phenyl]-2-yl)oxy)pyrrolidine-1-carboxylate (14a)

To a solution of 12 (0.50 g, 0.67 mmol) in dioxane/water (3:1 (v:v)) was added 1-cyclohexen-1-yl-boronic acid pinacol ester (0.17 g, 0.80 mmol), Pd(dppf)Cl$_2$ (0.025 g, 0.034 mmol), and Na$_2$CO$_3$ (0.14 g, 1.3 mmol). The reaction mixture was heated to 90° C. under argon and stirred for 24 h. The reaction mixture was cooled to room temperature, diluted with ethyl acetate, washed with water and brine, and dried over Na$_2$SO$_4$. The solid was then filtered, and the solution was concentrated under vacuum. The residue was purified by column chromatography to yield 13a as white solid (0.47 g).

Compound 13a (0.111 g, 0.15 mmol) was dissolved in EtOH/THF (20 mL). The air was evacuated and exchanged with argon three times and 10% Pd on activated carbon (0.017 g) was added. The argon was evacuated and exchanged with the H$_2$ gas three times and the reaction was allowed to stir under H$_2$ for 12 h. The mixture was filtered through celite and the solvent removed under reduced pressure to yield 14a (0.111 g, 94% yield over two steps) as off-white solid. $^1$H NMR (300 MHz, CDCl$_3$) δ 8.37 (d, J=35.9 Hz, 1H), 7.68 (t, J=32.1 Hz, 4H), 7.55-7.35 (m, 2H), 7.02 (d, J=13.6 Hz, 2H), 6.98-6.71 (m, 2H), 4.93 (s, 1H), 4.76 (s, 1H), 3.82-3.28 (m, 9H), 2.47-2.01 (m, 4H), 1.68 (d, J=5.4 Hz, 4H), 1.57 1.27 (m, 24H). $^{13}$C NMR (75 MHz, CDCl$_3$): δ ppm 165.71, 163.90, 160.63, 157.17, 154.75, 151.76, 150.66, 136.89, 136.01, 135.38, 134.06, 131.31, 129.13, 128.48, 127.66, 125.76, 123.77, 121.22, 115.19, 114.90, 113.07, 79.81, 51.81, 51.35, 44.34, 44.12, 34.48, 30.57, 29.04, 28.74, 25.89, 23.22, 22.38, 21.45.

tert-butyl (S)-3-((5-(4-(((S)-1-(tert-butoxycarbonyl) pyrrolidin-3-yl) oxy)-3-(4-(trifluoromethyl) cyclohexyl) benzamido)-4'-fluoro-[1,1'-biphenyl]-2-yl) oxy) pyrrolidine-1-carboxylate (14b)

The syntheses is the same as that of 14a to afford 14b as off-white solid (92% yield over two steps). $^1$H NMR (300 MHz, CDCl$_3$): δ ppm 8.43-8.09 (brm, 1H), 7.77-7.49 (m, 4H), 7.43-7.38 (m, 2H), 7.08-6.95 (m, 2H), 6.87 (d, J=8.7 Hz, 1H), 6.79 (dd, J=7.5, 16.6 Hz, 1H), 5.03-4.88 (brs, 1H), 4.74 (s, 1H), 3.64-3.29 (m, 8H), 2.97-2.76 (m, 1H), 2.42-2.18 (m, 3H), 2.08-1.58 (m, 10H), 1.44 (s, 9H), 1.42 (s, 9H). $^{13}$C NMR (75 MHz, CDCl$_3$): δ ppm 165.85, 163.85, 160.59, 157.29, 154.74, 150.70, 135.76, 134.02, 131.82, 131.26, 131.15, 127.03, 126.53, 123.84, 121.22, 115.77, 115.15, 114.87, 11.86, 79.91, 79.67, 75.80, 75.18, 51.71, 51.31, 44.28, 36.67, 31.68, 31.15, 28.69, 27.80, 27.44, 25.04, 24.31.

3-cyclohexyl-N-(4'-fluoro-6-(((S)-pyrrolidin-3-yl) oxy)-[1,1'-biphenyl]-3-yl)-4-(((S)-pyrrolidin-3-yl) oxy) benzamide dihydrochloride (1)

To a solution of 14a (0.37 g, 0.50 mmol) in CH$_2$Cl$_2$ (2 mL) under the anhydrous condition was added 4 M HCl in dioxane (10 mL). The mixture was then stirred at room temperature for 1-1.5 h. The solvent was removed under the reduced pressure to yield 3 as white solid (0.21 g, 68%). $^1$H NMR (500 MHz, CD$_3$OD) δ 8.01-7.77 (m, 2H), 7.69 (d, J=8.8 Hz, 2H), 7.65-7.41 (m, 2H), 7.32-7.11 (m, 3H), 7.07 (d, J=8.6 Hz, 1H), 5.32 (t, J=4.6 Hz, 1H), 5.05 (q, J=3.5 Hz, 1H), 3.70 (dd, J=13.2, 4.9 Hz, 1H), 3.63-3.36 (m, 6H), 3.17 (td, J=10.9, 7.9 Hz, 1H), 3.02 (tt, J=8.8, 3.4 Hz, 1H), 2.56-2.31 (m, 2H), 2.18 (ddd, J=10.6, 7.4, 3.9 Hz, 2H), 1.92-1.63 (m, 5H), 1.49 (td, J=10.4, 9.1, 3.3 Hz, 4H), 1.33 (dq, J=12.3, 4.4, 3.6 Hz, 1H). $^{13}$C NMR (126 MHz, CD$_3$OD) δ 167.05, 162.21 (d, J=245.3 Hz), 156.45, 150.05, 136.78, 134.10 (d, J=3.3 Hz), 133.38, 131.39, 131.04 (d, J=8.0 Hz), 127.45, 126.55 (d, J=16.2 Hz), 124.23, 121.81, 115.50, 114.62 (d, J=21.5 Hz), 111.59, 77.20, 75.68, 50.60, 50.45, 44.30, 44.05, 36.83, 32.92, 32.83, 30.84, 30.56, 26.67 (d, J=3.2 Hz), 25.99. HRMS (ESI) Calcd for C$_{33}$H$_{38}$FN$_3$O$_3$ (M+H)$^+$ 544.2975, found 544.2968.

N-(4'-fluoro-6-(((S)-pyrrolidin-3-yl) oxy)-[1,1'-biphenyl]-3-yl)-6-(((S)-pyrrolidin-3-yl) oxy)-2',3',4',5'-tetrahydro-[1,1'-biphenyl]-3-carboxamide dihydrochloride (2)

It was prepared through the same procedure as 1 to afford 2 as white solid (73% yield). $^1$H NMR (500 MHz, CD$_3$OD): δ ppm 7.87 (d, J=8.5 Hz, 1H), 7.76 (s, 1H), 7.66 (s, 2H), 7.52 (dd, J=5.5, 8.0 Hz, 2H), 7.17-7.04 (m, 4H), 5.76 (s, 1H), 5.24 (s, 1H) 5.02 (s, 1H), 3.73-3.63 (m, 2H), 3.57-3.35 (m, 7H), 3.15 (q, J=10.0 Hz, 1H), 2.33 (s, 4H), 2.16 (s, 4H), 1.78-1.63 (m, 4H). $^{13}$C NMR (125 MHz, CD$_3$OD): δ ppm 166.62, 163.10, 161.15, 156.51, 150.01, 136.33, 134.78, 134.00, 133.26, 131.24, 129.20, 127.64, 127.25, 126.97, 123.98, 121.59, 115.67, 115.02, 114.27, 113.40, 76.80, 72.96, 60.76, 50.36, 44.31, 30.89, 30.61, 28.78, 25.26, 22.73, 21.82. HRMS (ESI) Calcd for C$_{33}$H$_{36}$FN$_3$O$_3$ (M+H)$^+$ 542.2819, found 542.2803.

N-(4'-fluoro-6-(((S)-pyrrolidin-3-yl) oxy)-[1,1'-biphenyl]-3-yl)-4-(((S)-pyrrolidin-3-yl) oxy)-3-(4-(trifluoromethyl) cyclohexyl) benzamide dihydrochloride (3)

It was prepared through the same procedure as 1 to afford 3 as white solid (62% yield). $^1$H NMR (500 MHz, CD$_3$OD): δ ppm 7.90-7.82 (m, 2H), 7.71-7.63 (m, 2H), 7.57-7.51 (m, 2H), 7.18-7.11 (m, 3H), 7.09-7.05 (m, 1H), 5.32 (s, 1H), 5.03 (s, 1H), 3.74-3.62 (m, 2H), 3.58-3.44 (m, 6H), 3.41-3.36 (m, 1H), 3.20-2.99 (m, 2H), 2.48-2.30 (m, 3H), 2.17 (s, 2H), 2.04 (s, 2H), 1.91-1.79 (m, 3H), 1.75 (s, 1H). $^{13}$C NMR (125 MHz, CD$_3$OD): δ ppm 166.95, 163.12, 161.17, 156.59, 150.04, 135.52, 134.06, 133.27, 131.34, 130.80, 130.07, 127.84, 126.88, 124.10, 121.69, 115.73, 114.98, 114.31, 114.23, 111.77, 76.29, 72.14, 71.02, 60.75, 50.40, 44.23, 42.37, 35.25, 30.55, 27.48, 23.53. HRMS (ESI) Calcd for C$_{34}$H$_{37}$F$_4$N$_3$O$_3$ (M+H)$^+$ 612.2849, found 612.284.

Biochemical Characterization:

The biochemical AlphaScreen assay was employed to evaluate the inhibitory potency of these two final products for disruption of the β-catenin/BCL9 PPI. The results are shown in Table 1. Compound 2 exhibited an inhibition constant of 2.2±0.84 μM.

TABLE 1

The AlphaScreen K$_i$ values of 1 and 2. Each set of data was expressed as mean ± standard deviation (n = 3).

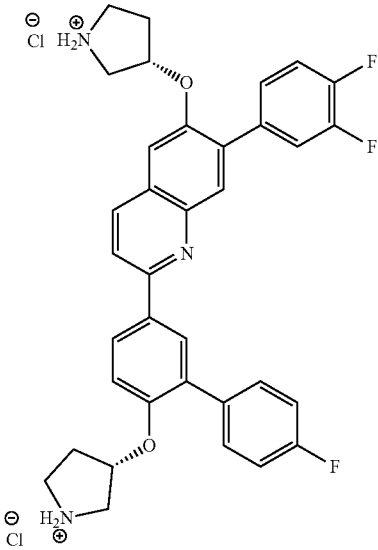 [SMILES: [Cl-] ; Fc1ccc(-c2cc(-c3ccc4cc(O[C@H]5CC[NH2+]C5)c(-c5ccc(F)c(F)c5)cc4n3)ccc2O[C@H]2CC[NH2+]C2)cc1 ; [Cl-]]

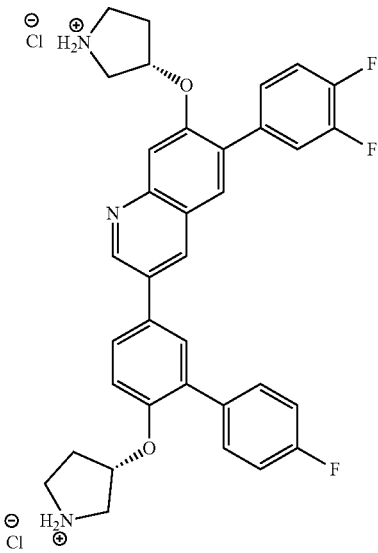 [SMILES: [Cl-] ; Fc1ccc(-c2cc(-c3cnc4cc(O[C@H]5CC[NH2+]C5)c(-c5ccc(F)c(F)c5)cc4c3)ccc2O[C@H]2CC[NH2+]C2)cc1 ; [Cl-]]

| No. | K$_i$ ± SD (μM) β-catenin/BCL9 |
|---|---|
| 1 | 8.0 ± 1.8 |
| 2 | 2.2 ± 0.84 |

The results for Compounds 3-5 are shown in Table 2. Compound 5 exhibited an inhibition constant of 4.2±2.3 μM.

TABLE 2

The AlphaScreen $K_i$ values of 1-5. Each set of data was expressed as mean ± standard deviation (n = 3).

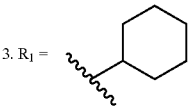 [SMILES: *C1CCCCC1]

| No. | $K_i$ ± SD (μM) β-catenin/BCL9 |
|---|---|
| 3 | 14 ± 1.6 |
| 4 | 7.1 ± 2.5 |
| 5 | 4.2 ± 2.3 |

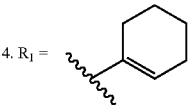 [SMILES: *C1=CCCCC1]

Protein expression and purification. Full-length β-catenin and (residues 1-781) were cloned into a pET-28b vector carrying a C-terminal 6× histidine (Novagen), and transformed into *E. coli* BL21 DE3 (Novagen). Cells were cultured in LB medium with 30 μg/mL kanamycin until the $OD_{600}$ was approximately 0.8, and then protein expression was induced with 400 μM of IPTG at 20° C. overnight. Cells were lysed by sonication. The proteins were purified by Ni-NTA affinity chromatography (30210, Qiagen) and dialyzed against a buffer containing 20 mM of Tris (pH 8.5), 100 mM NaCl, 10% glycerol, and 3 mM DTT. The purity of β-catenin was greater than 95% as determined by SDS-PAGE gel analysis. Native non-denaturing gel electrophoresis was performed to confirm the homogeneity of the purified proteins. Thermal-shift assay was performed on an iCycler iQ Real Time Detection System (Bio-Rad) to monitor protein stability and detect protein aggregation. Protein unfolding was evaluated through measuring the fluorescence changes of fluorescent dye Sypro Orange when interacting with wild-type or mutant β-catenin proteins. A temperature increment of 1°/min was applied. All proteins were stable and no aggregation was observed under storage or assay conditions. Proteins were aliquoted and stored at −80° C.

BCL9 Peptide Synthesis and Purification.

Human BCL9 (residues 350-375), N-terminally biotinylated human BCL9 (residues 350-375), A-terminally fluorescein-labeled human BCL9 (residues 350-375), and A-terminally biotinylated human E-cadherin (residues 824-877) were synthesized by InnoPep Inc. (San Diego, Calif., www.innopep.com). All synthesized peptides were purified by HPLC with purity >95%. The structures were validated by LC/MS. The sequences are as follows (Ahx, 6-aminohexanoic acid).

| Peptide | Sequence |
|---|---|
| Biotinylated BCL9 26-mer | Biotin-Ahx-$^{350}$GLSQEQLEHRERSL QTLRDIQRMLFP$^{375}$-NH$_2$ (SEQ ID NO.: 1, underlined portion) |

AlphaScreen assays. All experiments were performed in white opaque 384-well plates from PerkinElmer (Waltham, Mass.) with an assay buffer of 25 mM HEPES (pH=7.4), 100 mM NaCl, 0.1% BSA, and 0.01% Triton X-100. All sample signals were read on a Synergy 2 plate reader (Biotek, Winooski, Vt.) with a sensitivity setting of 200. The excitation wavelength was set at 680 nm and emission at 570 nm. All of the final reaction volumes were set to 25 μL. In the cross-titration experiments of the wild-type β-catenin/wild-type BCL9 interaction, N-terminally biotinlyated BCL9 (from 0 to 60 nM) and C-terminally $His_6$-tagged β-catenin (2.5, 5, 10, 20, 40, and 80 nM) were titrated in 20 μL assay buffer. After 2 h incubation at 4° C. on an orbital shaker, 2.5 μL of nickel chelate acceptor beads (10 μg/mL) and 2.5 μL of streptavidin-coated donor beads (10 μg/mL) were added. The mixture was then covered black and incubated at 4° C. for 1 h before detection. All addition and incubation was made under subdued lighting conditions due to the photosensitivity of the beads. The data were analyzed by nonlinear least-square analyses using GraphPad Prism 5.0. Each experiment was repeated three times, and the results were expressed as mean±standard deviation. The competitive binding experiments were performed to determine the apparent $K_d$ values. The rule of the competitive binding experiments for associating the $IC_{50}$ value with the $K_d$ value are: (1) the expected $K_d$ value should be 10 times higher than the concentration of either tested protein; (2) the concentrations of both tested proteins should be lower than the binding capacities of their respective beads; and (3) the concentration of the target protein ($His_6$-tagged β-catenin) should be 10 times lower than that of the ligand protein (biotinylated BCL9). In the competitive binding experiments to determine the $K_d$ value for β-catenin/BCL9 interactions, 5 nM of N-terminally biotinylated BCL9, 0.5 nM of C-terminally $His_6$-tagged β-catenin, and different concentrations of unlabeled BCL9 peptide (0-50 μM) were incubated at 4° C. in 20 μL assay buffer for 2 h. The donor and acceptor beads were added to a final concentration of 10 μg/mL in 25 μL assay buffer. The mixture was covered black and incubated for 1 h at 4° C. before detection. The $IC_{50}$ values, which were also the apparent $K_d$ values from the AlphaScreen assay, were determined by nonlinear least-square analyses using GraphPad Prism 5.0. Each experiment was repeated three times, and the results were expressed as mean±standard deviation.

For all of the competitive inhibition assays of β-catenin/BCL9 interactions, the negative control (equivalent to 0% inhibition) refers to 5.0 nM of biotinylated BCL9, 40 nM of His$_6$-tagged β-catenin, and 10 μg/mL of the donor and acceptor beads in a final volume of 25 μL assay buffer, but no tested inhibitor present. The positive control (equivalent to 100% inhibition) refers to 5.0 nM of biotinylated BCL9 and 10 μg/mL of the donor and acceptor beads in a final volume of 25 μL assay buffer.

For the β-catenin/BCL9 competitive inhibition assay, 5 nM of biotinylated BCL9 and 40 nM of His$_6$-tagged β-catenin were incubated in assay buffer at 4° C. for 30 min. Different concentrations of the tested inhibitor were added and incubated in 20 μL assay buffer at 4° C. for another 1 h. All of the above assay plates were covered and gently mixed on an orbital shaker. The donor and acceptor beads were then added to the plates to a final concentration of 10 μg/mL in 25 μL assay buffer. The mixture was incubated for 1 h at 4° C. before detection. The IC$_{50}$ value was determined by nonlinear least-square analysis of GraphPad Prism 5.0. The inhibition constant (K) values were derived from the IC$_{50}$ values using a method reported by Nikolovska-Coleska et al[26]. The assays were conducted under the conditions required by Nikolovska-Coleska et al.'s equation for determining the K$_i$ values. All of the experiments were performed in triplicate. The results were expressed as mean±standard deviation.

Cell-Based Characterization.

MTs cancer cell growth inhibition assays were conducted for 1-5. Three cancer cell lines with hyperactive Wnt/β-catenin signaling, SW480, HCT116, and MDA-MB-231. The half maximal inhibitory concentrations (IC$_{50}$) of these compounds are shown in Table 3.

MTs Cell Viability Assay.

Colorectal cancer cell lines, SW480 and HCT116, and PGP-40 T1 triple-negative breast cancer cell line MDA-MB-231 were seeded in 96-well plates at 4×10$^3$ cells/well, maintained overnight at 37° C., and incubated in the presence of 1 and 2 at various concentrations. Cell viability was monitored after 72 h using a freshly prepared mixture of 1 part phenazine methosulfate (PMS, Sigma) solution (0.92 mg/mL) and 19 parts 3-(4,5-dimethylthiazol-2-yl)-5-(3-carboxymethoxyphenyl)-2-(4-sulfophenyl)-2H-tetrazolium (MTs, Promega) solution (2 mg/mL). Cells were incubated in 10 μL of this solution at 37° C. for 3 h, and A$_{490}$ was measured. The effect of each compound is expressed as the concentration required to reduce A$_{490}$ by 50% (IC$_{50}$) relative to vehicle-treated cells. Experiments were performed in triplicate.

Cell Transfection and Luciferase Assay.

FuGENE6 (E269A, Promega) 96 well plate format was used for the transfection of HEK293 and SW480 cells according to the manufacturer's instruction. HEK293 cells were co-transfected with 45 ng of TOPFlash reporter gene, 135 ng pcDNA3.1-β-catenin, and 20 ng of pCMV-RL normalization reporter gene. SW480 cells were co-transfected with 60 ng of the TOPFlash or FOPFlash reporter gene and 40 ng of pCMV-RL normalization reporter. Cells were cultured in DMEM and 10% FBS at 37° C. for 24 h, and

TABLE 3

MTs growth inhibition assays to monitor the inhibitory activities of 1-5. Each set of data is expressed as mean ± standard deviation (n = 3). n.d. not determined.

| | MTs IC$_{50}$ ± SD (μM) | | | |
|---|---|---|---|---|
| | Wnt/β-catenin-hyperactive | | | Wnt-latent |
| No. | SW480 | HCT116 | MDA-MB-231 | A549 |
| 1 | 3.6 ± 1.9 | 9.6 ± 2.5 | 15 ± 6.1 | 23 ± 4.4 |
| 2 | 1.7 ± 0.90 | 2.2 ± 1.0 | 3.1 ± 1.2 | 7.5 ± 2.9 |
| 3 | 6.6 ± 2.7 | 3.8 ± 1.5 | n.d. | 3.8 ± 1.5 |
| 4 | 3.7 ± 2.0 | 6.9 ± 3.2 | 3.4 ± 1.6 | 8.9 ± 2.7 |
| 5 | 3.6 ± 2.7 | 5.6 ± 2.7 | 2.3 ± 1.0 | 4.8 ± 2.4 |

The TOPFlash luciferase reporter assay (in which the luciferase reporter has three wild-type Tcf4 binding sites) was performed with 1, 2, 4 and 5. These two compounds inhibited the TOPFlash luciferase activities, as shown in Table 4.

TABLE 4

Wnt-responsive TOPFlash (three wild-type Tcf binding sites) luciferase reporter assays of 1, 2, 4 and 5. Each set of data is expressed as mean ± standard deviation (n = 3). n.d. not determined.

| | TOPFlash IC$_{50}$ ± SD (μM) | |
|---|---|---|
| No. | β-catenin-activated HEK239 | SW480 |
| 1 | 26 ± 3.1 | 12 ± 1.5 |
| 2 | 14 ± 1.5 | 7.9 ± 1.4 |
| 4 | | 8.7 ± 2.3 |
| 5 | 10 ± 3.2 | 10 ± 3.3 | different concentrations of inhibitors or DMSO was added. After 24 h, the luciferase reporter activity was measured using the Dual-Glo system (E2940, Promega). Normalized luciferase activity in response to the treatment with 1 and 2 was compared with that obtained from the cells treated with DMSO. Experiments were performed in triplicate.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A compound having Formula IA or IB.

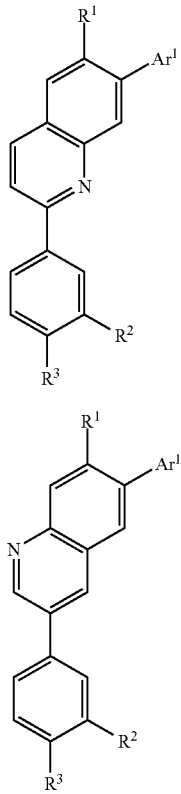

wherein
$R^1$ is selected from —$(C_2-C_8$ alkyl)-OH, —$(C_2-C_8$ alkyl)-$NH_2$, —O—$(C_2-C_8$ alkyl)-OH, —O—$(C_2-C_8$ alkyl)-$NH_2$, —NH—$(C_2-C_8$ alkyl)-OH, —NH—$(C_2-C_8$ alkyl)-$NH_2$, —NH-$Cy^1$, —NH-$Cy^2$, —O-$Cy^1$, —O-$Cy^2$, —$NHCH_2$-$Cy^1$, —$NHCH_2$-$Cy^2$, —$OCH_2$-$Cy^1$, and —$OCH_2$-$Cy^2$; wherein $Cy^1$, when present, is an amino $C_3$-$C_8$ cycloalkyl or hydroxy $C_3$-$C_8$ cycloalkyl, and wherein $Cy^1$ is substituted 0, 1, 2, or 3 groups independently selected from halogen, $C_1$-$C_4$ alkyl, $C_1$-$C_4$ monohaloalkyl, and $C_1$-$C_4$ polyhaloalkyl; and wherein $Cy^2$, when present, is a $C_2$-$C_7$ heterocycloalkyl comprising at least one oxygen or nitrogen atom, and wherein $Cy^2$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl;

$R^2$ is selected from $Ar^2$, —$A^1$—$A^2$—$Ar^2$, and —C≡C—$Ar^2$; wherein each of $A^1$ and $A^2$, when present, is independently selected from O, NH, and $CH_2$, provided that each of $A^1$ and $A^2$ is not simultaneously O; and wherein $Ar^2$ is selected from aryl and heteroaryl, and wherein $Ar^2$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, —$NHCOR^{20}$, —$NHSO_2R^{20}$, —$CONR^{21a}R^{21b}$, —$SO_2NR^{21a}R^{21b}$, —$CO_2H$, and tetrazole;

$R^3$ is selected from hydrogen, —$(C_2-C_8$ alkyl)-OH, —$(C_2$-$C_8$ alkyl)-$NH_2$, —O—$(C_2-C_8$ alkyl)-OH, —O—$(C_2-C_8$ alkyl)-$NH_2$, —NH—$(C_2-C_8$ alkyl)-OH, and —NH—$(C_2$-$C_8$ alkyl)-$NH_2$, —NH-$Cy^3$, —NH-$Cy^4$, —O—$Cy^3$, —O—$Cy^4$, —$NHCH_2$-$Cy^3$, —$NHCH_2$-$Cy^4$; —$OCH_2$-$Cy^3$, and —$OCH_2$-$Cy^4$; wherein $Cy^3$, when present, is an amino $C_3$-$C_8$ cycloalkyl or hydroxy $C_3$-$C_8$ cycloalkyl, and wherein $Cy^3$ is substituted 0, 1, 2, or 3 groups independently selected from halogen, $C_1$-$C_4$ alkyl, $C_1$-$C_4$ monohaloalkyl, and $C_1$-$C_4$ polyhaloalkyl; and wherein $Cy^4$, when present, is a $C_2$-$C_7$ heterocycloalkyl comprising at least one oxygen or nitrogen atom, and wherein $Cy^4$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl;

$Ar^1$ is selected from aryl and heteroaryl, and wherein $Ar^1$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, —$NHCOR^{20}$, —$NHSO_2R^{20}$, —$CONR^{21a}R^{21b}$, —$SO_2NR^{21a}R^{21b}$, —$CO_2H$, and tetrazole;

each occurrence of $R^{20}$, when present, is independently selected from $C_1$-$C_3$ alkyl, $C_1$-$C_3$ monohaloalkyl, $C_1$-$C_3$ polyhaloalkyl, and cyclopropyl;

each occurrence of $R^{21a}$ and $R^{21b}$, when present, is independently selected from hydrogen, $C_1$-$C_3$ alkyl, $C_1$-$C_3$ monohaloalkyl, $C_1$-$C_3$, and cyclopropyl;

or a pharmaceutically acceptable salt thereof.

2. The compound of claim 1, wherein $R^1$ is O-$Cy^2$.

3. The compound of claim 2, wherein $Cy^t$ is pyrrolidinyl substituted with 0, 1, 2, or 3 groups independently selected from halogen, $C_1$-$C_4$ alkyl, $C_1$-$C_4$ monohaloalkyl, and $C_1$-$C_4$ polyhaloalkyl.

4. The compound of claim 1, wherein $R^2$ is $Ar^2$ and $Ar^2$ is selected from phenyl substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$.

5. The compound of claim 1, wherein $R^3$ is O-$Cy^4$.

6. The compound of claim 5, wherein $Cy^4$ is pyrrolidinyl substituted with 0, 1, 2, or 3 groups independently selected from halogen, $C_1$-$C_4$ alkyl, $C_1$-$C_4$ monohaloalkyl, and $C_1$-$C_4$ polyhaloalkyl.

7. The compound of claim 1, wherein $Ar^1$ is selected from phenyl substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$.

8. A compound chosen from

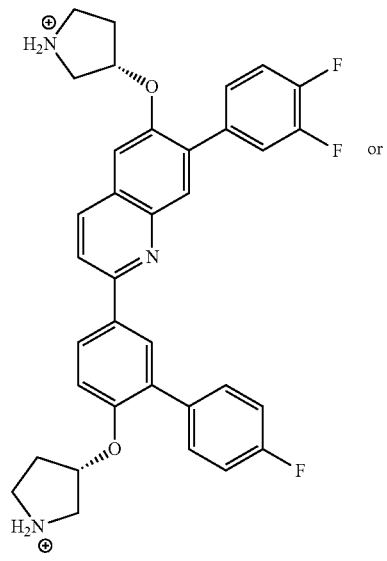

-continued
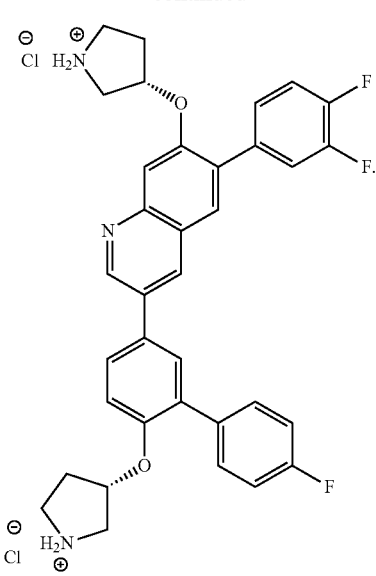
9. A method of inhibiting a β-catenin/BCL9 interaction in a cell comprising administering to the cell a compound of claim 1.
* * * * *